United States Patent
Nishihara et al.

(10) Patent No.: US 9,035,652 B2
(45) Date of Patent: May 19, 2015

(54) MAGNETIC RESONANCE IMAGING APPARATUS AND TWO-DIMENSIONAL EXCITATION ADJUSTMENT METHOD

(75) Inventors: Takashi Nishihara, Tokyo (JP); Hiroyuki Itagaki, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 524 days.

(21) Appl. No.: 13/504,590

(22) PCT Filed: Nov. 11, 2010

(86) PCT No.: PCT/JP2010/070080
§ 371 (c)(1),
(2), (4) Date: Apr. 27, 2012

(87) PCT Pub. No.: WO2011/059017
PCT Pub. Date: May 19, 2011

(65) Prior Publication Data
US 2012/0212223 A1    Aug. 23, 2012

(30) Foreign Application Priority Data
Nov. 12, 2009  (JP) ................................ 2009-258847

(51) Int. Cl.
*G01R 33/48* (2006.01)
*A61B 5/055* (2006.01)
(Continued)

(52) U.S. Cl.
CPC .............. *G01R 33/4828* (2013.01); *A61B 5/055* (2013.01); *A61B 5/4312* (2013.01); *A61B 5/7257* (2013.01); *G01R 33/4836* (2013.01)

(58) Field of Classification Search
CPC ........... G01R 33/4828; G01R 33/4836; A61B 5/055; A61B 5/4312; A61B 5/7257
See application file for complete search history.

(56) References Cited

U.S. PATENT DOCUMENTS 6,005,391 A * 12/1999 Bornert et al. ................. 324/309
6,025,716 A *  2/2000 Deimling ....................... 324/309
(Continued)

FOREIGN PATENT DOCUMENTS

JP    11-216124    8/1999
JP    11-225987    8/1999
(Continued)

OTHER PUBLICATIONS

International Search Report in PCT/JP2010/070080.
(Continued)

*Primary Examiner* — Dixomara Vargas
(74) *Attorney, Agent, or Firm* — Cooper & Dunham LLP

(57) ABSTRACT

An MRI apparatus and a two-dimensional excitation adjustment method capable of performing appropriately two-dimensional excitation of a region, in which materials with different resonance frequencies are present, according to imaging conditions are provided. In order to do so, when performing the two-dimensional excitation of a two-dimensional excitation region of an object formed by a first material with a first resonance frequency and a second material with a second resonance frequency, an irradiation frequency of a high-frequency magnetic field for the two-dimensional excitation is set on the basis of the imaging conditions related to the two-dimensional excitation and the first and second resonance frequencies so that desired regions of the first and second materials are excited in a two-dimensional manner.

17 Claims, 20 Drawing Sheets

(51) Int. Cl.
  *A61B 5/00*     (2006.01)
  *G01R 33/483*   (2006.01)

(56) References Cited

U.S. PATENT DOCUMENTS

| | | | |
|---|---|---|---|
| 6,373,249 B1 * | 4/2002 | Kwok et al. | 324/306 |
| 6,445,182 B1 * | 9/2002 | Dean et al. | 324/309 |
| 6,541,971 B1 * | 4/2003 | Dannels | 324/309 |
| 6,696,889 B2 * | 2/2004 | Watanabe | 329/309 |
| 6,980,001 B2 * | 12/2005 | Paley et al. | 324/318 |
| 6,995,559 B2 * | 2/2006 | Agilandam et al. | 324/309 |
| 7,560,924 B2 * | 7/2009 | Kanda | 324/307 |
| 7,800,368 B2 * | 9/2010 | Vaughan et al. | 324/318 |
| 8,831,703 B2 * | 9/2014 | van der Kouwe et al. | 600/410 |
| 2003/0055329 A1 | 3/2003 | Zur | |

FOREIGN PATENT DOCUMENTS

| | | |
|---|---|---|
| JP | 2001-95773 | 4/2001 |
| JP | 2003-52667 | 2/2003 |
| JP | 2003-190114 | 7/2003 |
| JP | 2008-54738 | 3/2008 |

OTHER PUBLICATIONS

Araki, Tsutomu (2008), Ketteiban MRI Kanzen Kaisetsu, $1^{st}$ edition, p. 501.

* cited by examiner

MAGNETIC RESONANCE IMAGING APPARATUS AND TWO-DIMENSIONAL EXCITATION ADJUSTMENT METHOD

TECHNICAL FIELD

The present invention relates to a magnetic resonance imaging (hereinafter, referred to as "MRI") technique and in particular, to an imaging technique based on two-dimensional excitation in which a region restricted in an arbitrary two-dimensional direction is selectively excited.

BACKGROUND ART

An MRI apparatus is an apparatus which measures an NMR signal generated by an object, especially, nuclear spins which form human tissue, and images the shapes or functions of the head, abdomen, limbs, and the like in a two-dimensional manner or in a three-dimensional manner. In the imaging, different phase encoding is given to the NMR signals by a gradient magnetic field and frequency encoding is also given to the NMR signals, and the NMR signals are measured as time-series data. The measured NMR signals are reconstructed as an image by two-dimensional or three-dimensional Fourier transform.

Generally, in the MRI apparatus, only a one-dimensional direction of the object is specified and an arbitrary planar region with a predetermined thickness is selectively excited using a high-frequency magnetic field (hereinafter, referred to as an RF) and the gradient magnetic field. In contrast, there is a two-dimensional spatial selective excitation (spectral-spatial; hereinafter, referred to as SS) method of specifying two directions instead of the entire planar region and exciting selectively only the inside of a region limited by the two directions (for example, refer to NPL 1). In the SS method, in order to realize such two-dimensional spatial selective excitation (hereinafter, simply referred to as two-dimensional excitation), waveforms of the RF and the gradient magnetic field are calculated on the basis of a profile of an excitation region, and the calculated RF for the two-dimensional excitation (hereinafter, referred to as a 2DRF) is applied together with an oscillating gradient magnetic field.

Since a signal can be acquired by exciting only the inside of the region selected by restriction in the two-dimensional direction in the SS method, a signal from the outside of the region can be effectively suppressed. For example, this SS method is used for a navigator echo sequence (hereinafter, referred to as navi-echo) for tracking the movement of the diaphragm (for example, refer to NPL 2). In the navi-echo, the vicinity of the diaphragm is excited in a cylindrical shape in a body axis direction using the SS method, and a temporal change of a diaphragm position in a cylinder axis direction of a region excited in the cylindrical shape is detected from echo signals generated from the region to thereby monitor a respiratory motion.

RELATED ART LITERATURE

Non Patent Literature

[NPL 1] A K-Space Analysis of Small-Tip-Angle Excitation, J. Pauly, D. Nishimura, J. Magn. Reson., 81, 43-56 (1989)
[NPL 2] Navigator-Echo-based Real-Time Respiratory Gating and Triggering for Reduction of Respiration Effects in Three-dimensional Coronary MR Angiography, Yi Wang, et al, Radiology, 198, 55-60 (1996)
[NPL 3] Techniques and Clinical Applications of Flow Prep method, IFIR method, and IR-IFIS method, Masayoshi Sugimura, INNERVISION, Vol. 23(9), 43-45 (2008)

OUTLINE OF INVENTION

Problems to be Solved by the Invention

Main objects to be imaged by MRI are two types, water and fat. Resonance frequencies of protons of water and fat are different. In an MRI apparatus with a static magnetic field strength of 1.5 [T], there is a difference of 224 [Hz] between the resonance frequencies of water and fat. Accordingly, if an irradiation frequency of the RF is set as the resonance frequency of one of water and fat, the resonance frequency of the other one and the irradiation frequency of the RF are shifted by 224 [Hz]. Hereinafter, a shift between the resonance frequency of nuclear magnetization and the irradiation frequency of the RF is assumed to be $\Delta F$. The influence of $\Delta F$ of about 224 [Hz] on an excitation profile is particularly large in the case of the 2DRF. For example, when exciting a cylindrical region with Duration of 8 [ms], the number of revolutions in a k space of 10, a flip angle (hereinafter, FA) of 90 [deg], and a diameter (hereinafter, $\phi$) of 30 [mm], the cylindrical shape changes to the shape of a concentric circle in which $\phi$ is about 130 [mm], and the FA changes to about 45 [deg] (50%). The influence of changes in $\phi$ and FA of the 2DRF on an image is great.

As a specific example to which the 2DRF is applied, suppression of the heart in chest imaging may be mentioned. For example, when the irradiation frequency of the 2DRF is set as the resonance frequency of water in order to suppress only the heart, a water component of the heart is suppressed to $\phi=30$ [mm], but fat is suppressed in the concentric circle shape of $\phi=130$ [mm]. As a result, since the heart to be suppressed and the thymus gland or the breast to be imaged are located close to each other in the chest, fat of the thymus gland or the breast to be imaged is suppressed, but a fat component of the heart is not suppressed conversely.

Therefore, it is an object of the present invention to provide an MRI apparatus and a two-dimensional excitation adjustment method capable of performing appropriately two-dimensional excitation of a region, in which materials with different resonance frequencies are present, according to imaging conditions.

Means for Solving the Problems

In the present invention, in order to achieve the above-described object, when performing two-dimensional excitation of a two-dimensional excitation region of an object formed by a first material with a first resonance frequency and a second material with a second resonance frequency, an irradiation frequency of a high-frequency magnetic field for the two-dimensional excitation is set on the basis of imaging conditions related to the two-dimensional excitation and the first and second resonance frequencies so that desired regions of the first and second materials are excited in a two-dimensional manner.

Specifically, an MRI apparatus of the present invention includes a control unit that controls measurement of an echo signal, which is generated from a two-dimensional excitation region of an object placed in a static magnetic field, using a pulse sequence with a high-frequency magnetic field and a gradient magnetic field for performing two-dimensional excitation of the two-dimensional excitation region of the object, and is characterized in that the object is formed by a first material with a first resonance frequency and a second material with a second resonance frequency and the control unit includes an irradiation frequency setting section which sets an irradiation frequency of the high-frequency magnetic field for the two-dimensional excitation on the basis of imaging conditions related to the two-dimensional excitation and the first and second resonance frequencies so that desired regions of the first and second materials are excited in a two-dimensional manner.

In addition, a two-dimensional excitation adjustment method of the present invention is characterized in that when performing two-dimensional excitation of a two-dimensional excitation region of an object formed by a first material with a first resonance frequency and a second material with a second resonance frequency, it includes: an input step which inputs imaging conditions related to the two-dimensional excitation; a step which calculates the first and second resonance frequencies; and a step which sets an irradiation frequency of a high-frequency magnetic field for two-dimensional excitation on the basis of the imaging conditions related to the two-dimensional excitation and the first and second resonance frequencies so that desired regions of the first and second materials are excited in a two-dimensional manner.

Advantage of the Invention

According to an MRI apparatus and a two-dimensional excitation adjustment method of the present invention, it becomes possible to appropriately perform two-dimensional excitation of a region, in which materials with different resonance frequencies are present, according to imaging conditions.

MODE FOR CARRYING OUT THE INVENTION

Figure 1:
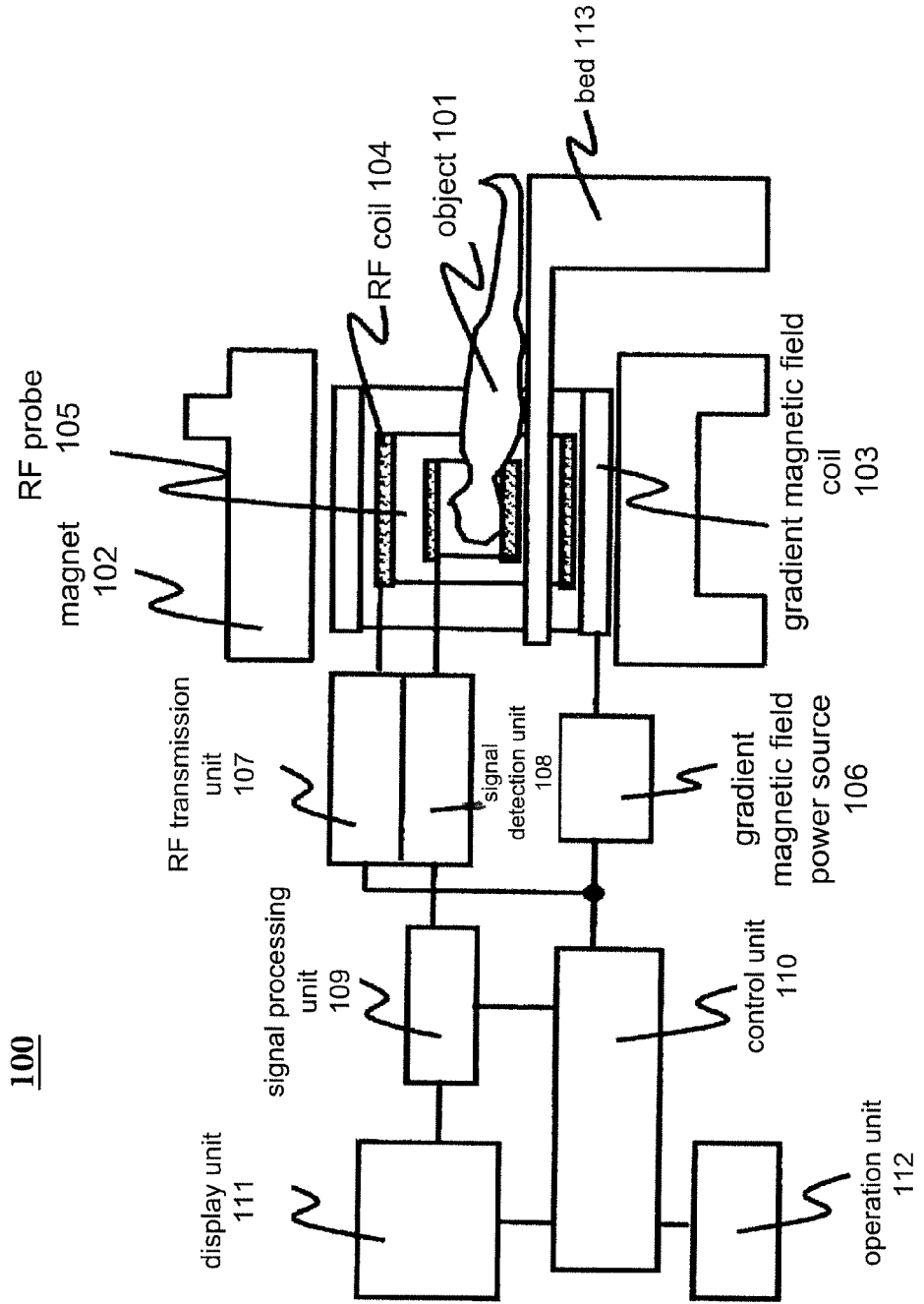
FIG. 1 is an example of a functional block diagram of an MRI apparatus related to the present invention.

Hereinafter, preferred embodiments of an MRI apparatus and a two-dimensional excitation adjustment method of the present invention will be described in detail according to the accompanying drawings. In addition, in all drawings for explaining the embodiments of the present invention, the same reference numerals are given to those with the same functions and repeated explanation thereof will be omitted.

First, the outline of an example of the MRI apparatus related to the present invention will be described on the basis of FIG. 1. FIG. 1 is a functional block diagram of an MRI apparatus 100 related to the present invention. The MRI apparatus 100 related to the present invention includes a magnet 102, a gradient magnetic field coil 103, a high-frequency magnetic field (RF) irradiation coil 104, an RF receiving coil 105, a gradient magnetic field power source 106, an RF transmission unit 107, a signal detection unit 108, a signal processing unit 109, a control unit 110, a display unit 111, an operation unit 112, and a bed 113.

The magnet 102 generates a static magnetic field in a region (inspection space) around an object 101. The gradient magnetic field coil 103 is formed by coils in three directions of X, Y, and Z, and generates a gradient magnetic field in the inspection space according to a signal from the gradient magnetic field power source 106. The RF irradiation coil 104 applies (emits) an RF to the inspection space according to a signal from the RF transmission unit 107. The RF receiving coil 105 detects an echo signal generated by the object 101. The echo signal received by the RF receiving coil 105 is detected by the signal detection unit 108, is subjected to signal processing by the signal processing unit 109, and is input to the control unit 110. The control unit 110 reconstructs an image from the input echo signal and displays it on the display unit 111. In addition, the control unit 110 controls the operations of the gradient magnetic field power source 106, the RF transmission unit 107, and the signal detection unit 108 according to a time chart of control stored in advance and imaging parameters input by an operator through the operation unit 112. In addition, the time chart of control is generally called a pulse sequence. The bed 113 is for taking the object 101 into the inspection space or taking out the object 101 from the inspection space in a state where the object 101 lies thereon.

In addition, the MRI apparatus 100 may further include a shim coil for correcting the non-uniformity of the static magnetic field of the inspection space and a shim power source for supplying a current to the shim coil.

A current target to be imaged by the MRI is a proton of water or fat which are main components of the object 101. The shapes or functions of the head, abdomen, limbs, and the like of a human body are imaged in a two-dimensional or three-dimensional manner by imaging a spatial distribution of proton density or a spatial distribution of relaxation of an excited proton.

Figure 2:
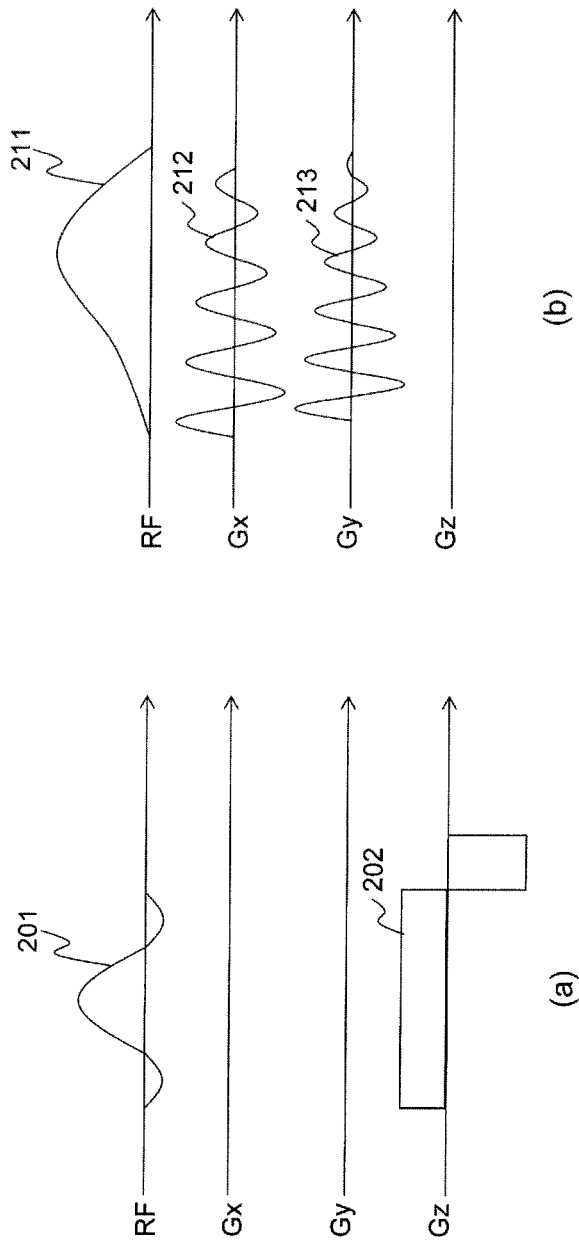
FIG. 2(a) is a pulse sequence diagram based on a conventional excitation method.
FIG. 2(b) is a pulse sequence diagram based on an SS method of a first embodiment.

In the present embodiment, an SS (Spectral-Spatial) method of exciting a predetermined spatial region selectively is used for imaging. Here, a pulse sequence of the SS method will be described by comparing it with a pulse sequence in a conventional excitation method. FIG. 2 is a view for explaining an example of the pulse sequence based on the SS method related to the present invention by comparing it with the pulse sequence based on the conventional excitation method. FIG. 2(a) shows the pulse sequence based on the conventional excitation method, and FIG. 2(b) shows the pulse sequence based on the SS method used in the present embodiment.

As the conventional method, an example of exciting selectively an arbitrary slice for which only a position in the z-axis direction is specified is shown. In addition, in the SS method, an example is shown in which an arbitrary columnar region, for which only the shape on an xy plane is specified, is selectively excited. Here, the shape specified on the xy plane is assumed to be a circle. Moreover, in a pulse sequence diagram of this specification, RF, Gx, Gy, and Gz are timing charts of application of a high-frequency magnetic field (RF) pulse, a gradient magnetic field in the x-axis direction, a gradient magnetic field in the y-axis direction, and a gradient magnetic field in the z direction, respectively.

As shown in FIG. 2(a), in the conventional method, a slice selection gradient magnetic field (Gz) 202 which is fixed in the z-axis direction is given at the time of application of an RF 201. Accordingly, a predetermined planar region (slice) for which only the position in the z-axis direction is specified is selectively excited. On the other hand, in the SS method, an RF (2DRF) 211 is applied together with a vibration gradient magnetic field (Gx) 212 in the x-axis direction and a vibration gradient magnetic field (Gy) 213 in the y-axis direction, as shown in FIG. 2(b). Accordingly, a cylindrical region with an axis parallel to a z axis is selectively excited. In any method, phase encoding is applied to echo signals obtained from the excited region, and the echo signals are sampled in time series and are disposed in a k space. An image is obtained by performing a Fourier transform on the echo signals (data) disposed in the k space. Here, as the number of phase encoding, a value of 128, 256, 512, or the like per image is usually selected. In addition, a value of 128, 256, 512, or 1024 is selected as the sampling number.

Next, the outline of the MRI apparatus and the two-dimensional excitation adjustment method related to the present invention will be described. In the present invention, when placing an object including first and second materials with different resonance frequencies within the static magnetic field and measuring echo signals generated from the object using a pulse sequence with a high-frequency magnetic field (2DRF) and a gradient magnetic field for performing desired two-dimensional excitation, the high-frequency magnetic field is adjusted such that desired regions of the first and second materials are excited in a two-dimensional manner on the basis of imaging conditions related to two-dimensional excitation and the resonance frequencies of the first and second materials. By irradiating the object with the adjusted high-frequency magnetic field, the echo signals are measured.

Figure 3:
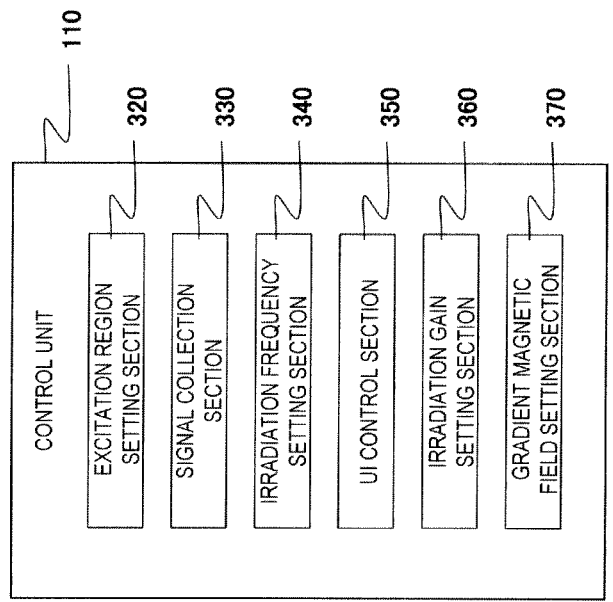
FIG. 3 is a functional block diagram of a control unit of the first embodiment.

Therefore, the control unit 110 of the MRI apparatus 100 related to the present invention has a functional block shown in FIG. 3 to realize processing for adjusting the high-frequency magnetic field for two-dimensional excitation (2DRF). That is, as shown in FIG. 3, the control unit 110 includes: an excitation region setting section 320 which sets an imaging parameter according to the pulse sequence set in advance so as to excite a two-dimensional selection region set by the operator; a signal collection section 330 which executes the pulse sequence to acquire echo signals from the two-dimensional selection region; an irradiation frequency setting section 340 which adjusts and sets an irradiation frequency for 2DRF for exciting the two-dimensional selection region; a UI control section 350 which controls the display of a UI screen for setting the two-dimensional selection region on the display unit 111; an irradiation gain setting section 360 which adjusts and sets an irradiation gain (that is, a gain of an RF amplifier) of the 2DRF for exciting the two-dimensional selection region; and a gradient magnetic field setting section 370 which adjusts and sets the gradient magnetic field applied together with the 2DRF for exciting the two-dimensional selection region. In addition, the control unit 110 of the present invention includes a CPU, a memory, and a storage device, and each of the functions described above is realized when the CPU loads a program stored in the storage device to the memory and executes it.

When adjusting the high-frequency magnetic field, echo signals are actually collected from the two-dimensional excitation region of the object, a 2DRF appropriate for the two-dimensional excitation of the region is determined using the result, and the determined 2DRF is irradiated to the object. Hereinafter, this processing is called high-frequency magnetic field adjustment processing. In addition, an irradiation frequency determined in the conventional method, that is, an irradiation frequency determined on the basis of echo signals obtained from the entire imaging region is used as the irradiation frequency of an RF applied at the time of echo signal collection in the high-frequency magnetic field adjustment processing.

Hereinafter, each embodiment of the MRI apparatus and the two-dimensional excitation adjustment method related to the present invention will be described using a proton of water (hereinafter, also simply referred to as water) as an example of the first material and a proton of fat (hereinafter, also simply referred to as fat) as an example of the second material. However, the present invention may also be applied to the case of two or more materials with different resonance frequencies without being limited to water and fat.

Figure 5:
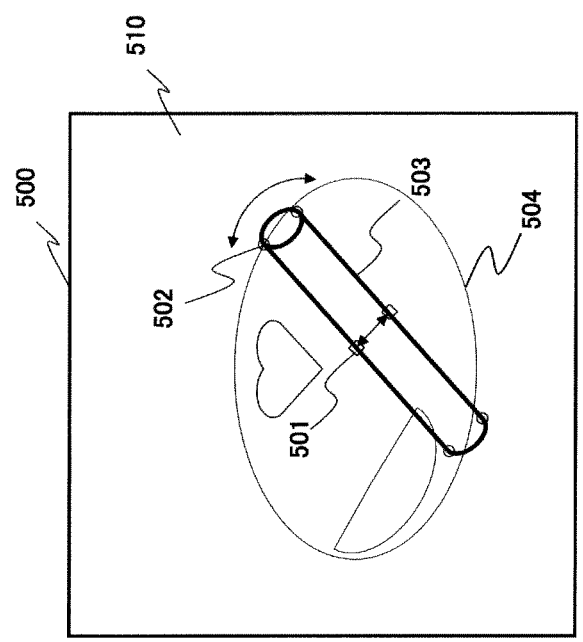
FIG. 5 is an explanatory view of a UI screen of the first embodiment.

In addition, a two-dimensional cylindrical region shown in FIG. 5 is assumed as a desired two-dimensional excitation region, a diameter φ 501 of a cylinder is designated as a parameter indicating the shape. In addition, the length of the cylindrical region in its long axis direction is arbitrary, and is not particularly limited. In addition, an FA (Flip Angle) is designated as a parameter indicating the flip angle of the two-dimensional excitation region. However, the two-dimensional excitation region related to the present invention is not limited to the two-dimensional cylindrical region, and a region with an arbitrary shape is possible.

First Embodiment

Next, a first embodiment of the MRI apparatus and the two-dimensional excitation adjustment method related to the present invention will be described. In the present embodiment, the two-dimensional excitation is performed using a high-frequency magnetic field having as its irradiation frequency an average value of a resonance frequency of a proton of water (first material) and a resonance frequency of a proton of fat (second material). In addition, in the present embodiment, both an excitation region of water and an excitation region of fat are two-dimensional cylindrical regions which are at the same position and have the same diameter $\phi$, and both the flip angle of the excitation region of water and the flip angle of the excitation region of fat are set as the same angle FA. Hereinafter, the configuration and procedure of the MRI apparatus 100 of the present embodiment will be described.

First, the process flow of the high-frequency magnetic field adjustment processing for 2DRF of the present embodiment will be described on the basis of FIG. 4. Moreover, in advance of this irradiation frequency adjustment processing, an overall irradiation frequency F0 is determined from signals of the entire imaging region in the conventional method.

In step 401, the UI control section 350 displays the UI screen on the display unit 111 to receive an input regarding the setting of the position, shape, and flip angle FA of a region which the operator wants to image and/or a two-dimensional excitation region. On the UI screen, the operator inputs the setting of the position, shape, and flip angle FA of the region which the operator wants to image and/or the two-dimensional excitation region. When the input of the imaging region and/or the two-dimensional excitation region is received through the UI screen, the UI control section 350 notifies the excitation region setting section 320 of the corresponding region.

Specifically, the UI control section 350 displays a UI screen 500 for setting the position and shape of the two-dimensional excitation region, which is shown in FIG. 5, on the display unit 111. A positioning image 510 acquired in advance is displayed on the UI screen 500 shown in FIG. 5. In addition, a handle 501 capable of setting the diameter $\phi$ of the cylindrical region which is the two-dimensional excitation region, a handle 502 capable of setting the two-dimensional excitation region to have an arbitrary angle, a handle 503 capable of setting the two-dimensional excitation region at an arbitrary position are displayed on the positioning image 510. The operator sets a desired cylindrical region by operating these handles. In addition, the diameter $\phi$ and the flip angle FA of the cylindrical region which is the two-dimensional excitation region may be fixed values stored in advance in the MRI apparatus. In addition, since the cross-sectional shape of the two-dimensional excitation region in the present embodiment can be set arbitrarily, the cross-sectional shape is not limited to a circle.

In step 402, a prescan of the two-dimensional excitation region set in step 401 is performed to measure a spectral distribution of a resonance frequency in the two-dimensional excitation region.

Figure 6:
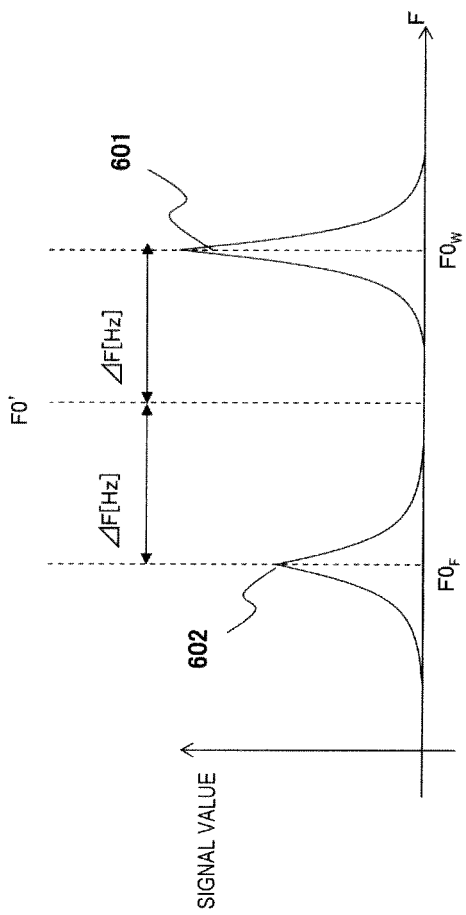
FIG. 6 is a view showing a spectral distribution of a resonance frequency in the first embodiment.

Specifically, the excitation region setting section 320 sets an imaging parameter so as to excite the two-dimensional excitation region set in step 401 according to the pulse sequence set in advance. In this case, the overall irradiation frequency F0 is used as the irradiation frequency of the RF. Next, the signal collection section 330 executes the above-described pulse sequence with the set imaging parameter (prescan) to acquire echo signals from the two-dimensional excitation region. In this case, the echo signals are acquired without phase encoding or slice encoding. In addition, the irradiation frequency setting section 340 performs a Fourier transform (FT) of the echo signals from the two-dimensional excitation region in a time direction. As a result, a resonance frequency (spectrum) distribution in the two-dimensional excitation region is acquired. An example of this spectral distribution is shown in FIG. 6. By limiting the excitation by prescan to the two-dimensional excitation region, the influence of the non-uniformity of the static magnetic field can also be eliminated.

In step 403, the irradiation frequency setting section 340 determines resonance frequencies $F0_W$ and $F0_F$ of water and fat on the basis of the spectral distribution generated in step 402.

Specifically, since protons to be imaged, among protons which form the object, are mainly protons of water and fat, a peak 601 present at the high frequency side in the spectral distribution is set as the resonance frequency $F0_W$ of a proton of water and a peak 602 present at the low frequency side is set as the resonance frequency $F0_F$ of a proton of fat. Alternatively, $F0_W$ and $F0_F$ may also be determined from a gyromagnetic ratio $\gamma$ [Hz/T] of the proton of water and a static magnetic field strength B0 [T]. For example, a peak of the spectral distribution closest to a resonance frequency $\gamma B0$ [Hz] of the proton of water is set as $F0_W$. In addition, since a chemical shift $\alpha$ of the proton of water and the proton of fat is 3.5 [ppm], a peak of the spectral distribution closest to $F0_W - \alpha \gamma B0$ [Hz] is set as $F0_F$. In addition, although the MRI apparatus may determine $F0_W$ and $F0_F$ automatically as described above, the irradiation frequency setting section 340 may display the spectral distribution shown in FIG. 6 on the display unit 111 and receive the operator's setting input. That is, the operator may determine $F0_W$ and $F0_F$.

In step 404, the irradiation frequency setting section 340 calculates an irradiation frequency of the high-frequency magnetic field (2DRF) for exciting the two-dimensional excitation region set in step 401. Specifically, the irradiation frequency setting section 340 calculates an average value F0' of $F0_W$ and $F0_F$ determined in step 403 using the following Expression and sets it as the irradiation frequency of the 2DRF.

$$F0'=(F0_W+F0_F)/2 \quad (1)$$

In step 405, on the basis of the irradiation frequency F0' of the 2DRF calculated in step 404, the irradiation gain setting section 360 calculates an irradiation gain for the flip angle FA and the gradient magnetic field setting section 370 calculates an appropriate gradient magnetic field strength, so that the two-dimensional excitation region with the cylinder diameter $\phi$ set in step 401 is excited by the flip angle FA.

Figure 7:
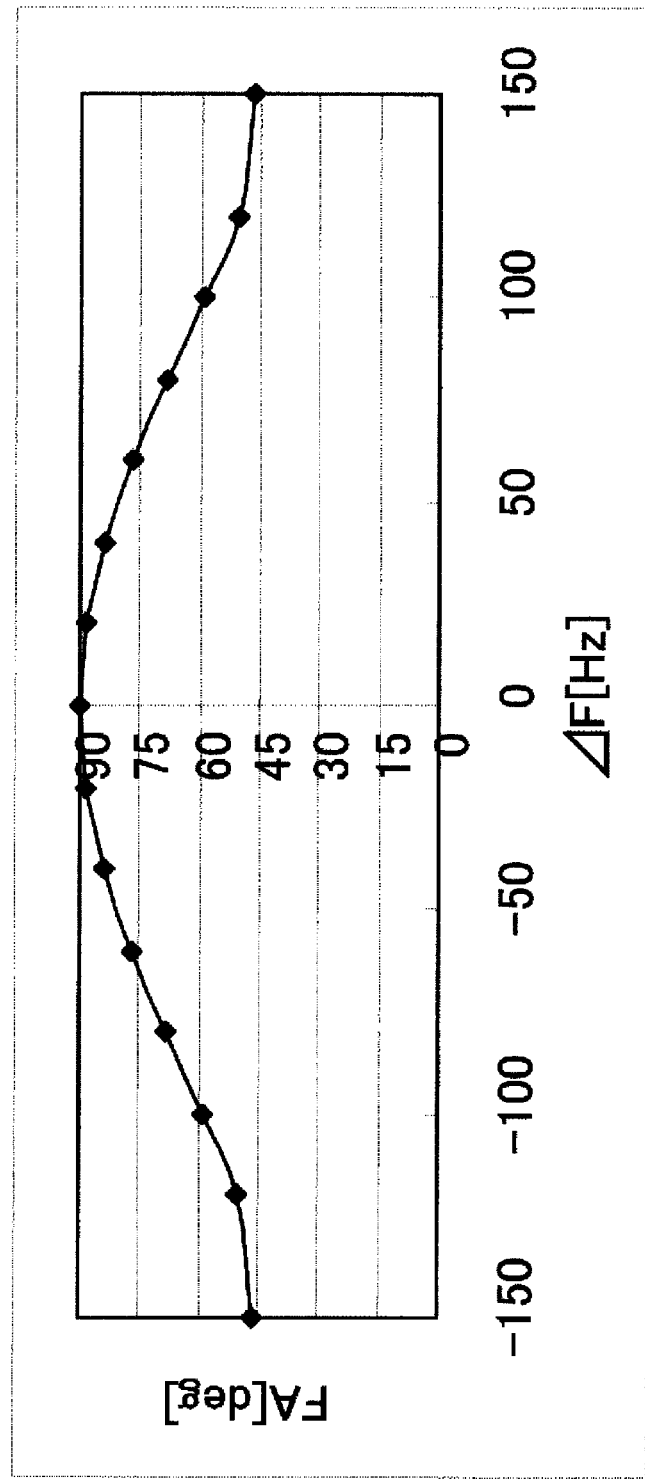
FIG. 7 is a graph showing the relationship between ΔF and FA of the first embodiment.
Figure 8:
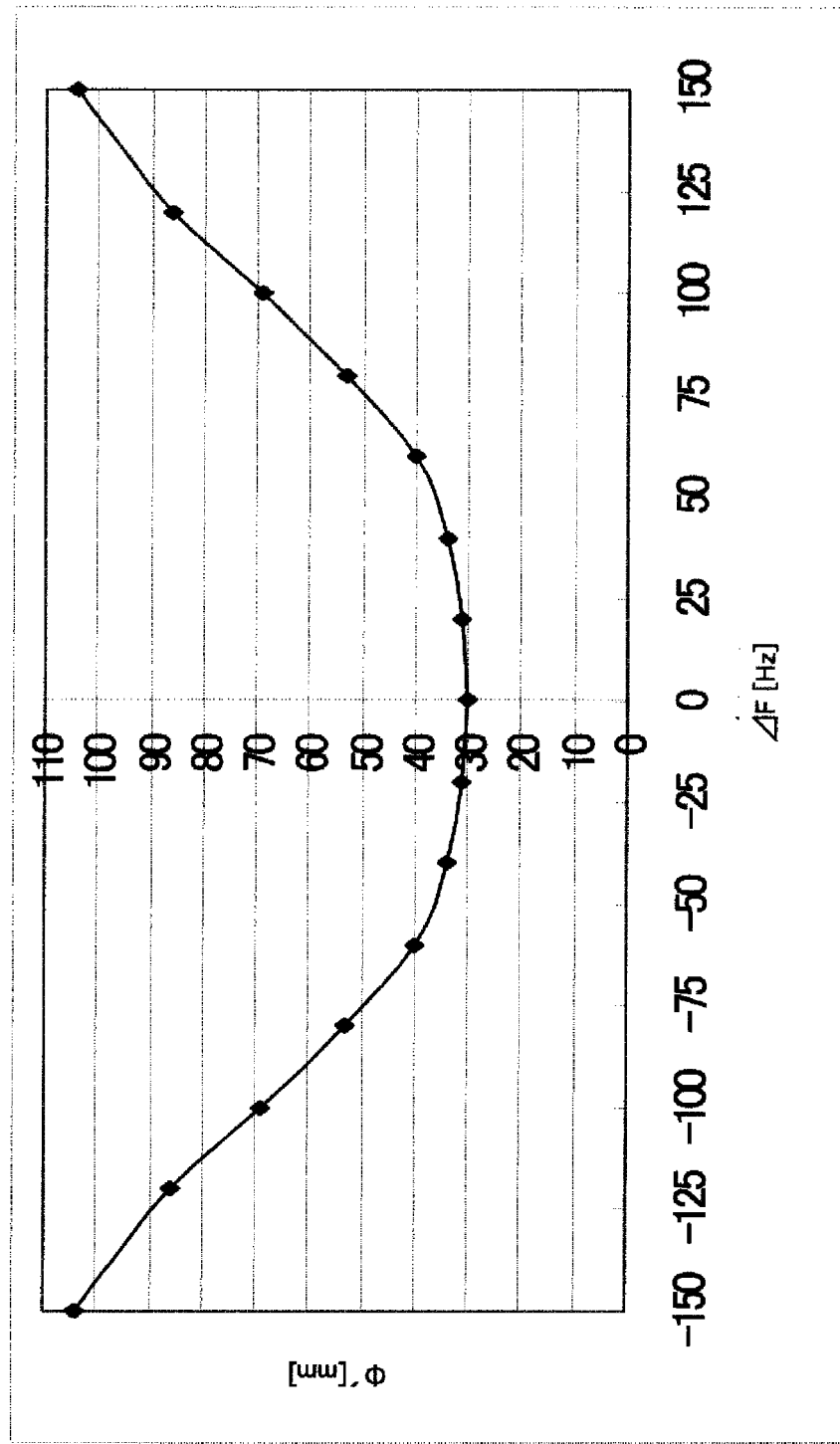
FIG. 8 is a graph showing the relationship between ΔF and φ of the first embodiment.

Specifically, a difference between the resonance frequency $F0_W$ of the proton of water and the irradiation frequency F0' of the 2DRF is set to $\Delta F$. $\Delta F$ and the flip angle FA satisfy the relationship shown in FIG. 7, and $\Delta F$ and the cylinder diameter $\phi$ satisfy the relationship shown in FIG. 8. The relationships shown in FIGS. 7 and 8 are determined depending on the irradiation time (Duration) of 2DRF, FA, $\phi$, and a k space trajectory. As shown in FIGS. 7 and 8, changes of $\phi$ and FA are symmetrical with respect to $\Delta F$=0. Since F0' is an average value of $F0_W$ and $F0_F$, both an absolute value of the difference between the irradiation frequency F0' and the resonance frequency $F0_W$ of the proton of water and an absolute value of a difference between the irradiation frequency F0' and the resonance frequency $F0_F$ of the proton of fat are the same value $|\Delta F|$.

Therefore, assuming that FIG. 7 is a function FA'($\Delta F$) of a flip angle FA' with respect to $\Delta F$ and FIG. 8 is a function $\phi'$($\Delta F$) of a cylinder diameter $\phi''$ with respect to $\Delta F$, a cylinder diameter $\phi'$ and the flip angle FA' when the resonance frequency changes by $\Delta F$ can be determined if $\Delta F$ is determined.

When $F0_W$ is set as the irradiation frequency of the 2DRF, a gradient magnetic field strength required to set the cylinder diameter, which is the two-dimensional excitation region, to φ is set to $G_W$ and an irradiation gain required to set the flip angle to FA is set to $T_W$. In addition, when F0' is set as the irradiation frequency of the 2DRF, a gradient magnetic field strength $G_W$' required to set the cylinder diameter to φ and an irradiation gain $T_W$' required to set the flip angle to FA can be calculated by the following Expression.

$$G_W' = G_W * \phi'/\phi \quad (2)$$

$$T_W' = T_W * FA/FA' \quad (3)$$

Then, the gradient magnetic field setting section 370 calculates the gradient magnetic field strength $G_W$' on the basis of Expression (2) described above and the irradiation gain setting section 360 calculates the irradiation gain $T_W$' on the basis of Expression (3) described above, and each of the irradiation gain setting section 360 and the gradient magnetic field setting section 370 notifies the calculation result to the signal collection section 330.

In step 406, the signal collection section 330 sets the irradiation frequency of the 2DRF calculated in step 404 to F0', and performs imaging of a desired region using the pulse sequence by which the irradiation gain $T_W$' and the gradient magnetic field strength $G_W$' calculated in step 405 are set.

In particular, if the two-dimensional excitation region set in step 401 is excited as a prepulse, a prepulse sequence is executed for the two-dimensional excitation region using the 2DRF having F0' as an irradiation frequency of a high-frequency magnetic field for prepulse, the gradient magnetic field strength $G_W$', and the irradiation gain $T_W$'. Accordingly, both a water region and a fat region are excited in a state where the position, the shape, and the flip angle are substantially the same. In addition, the resonance frequency F0 determined from signals of the entire imaging region is set as an irradiation frequency of a high-frequency magnetic field in a main pulse sequence subsequent to the prepulse sequence.

The above is an explanation regarding the process flow of the present embodiment.

As described above, according to the MRI apparatus and the two-dimensional excitation adjustment method of the present embodiment, the two-dimensional excitation is performed using the high-frequency magnetic field having as its irradiation frequency the average value of the resonance frequency of the first material and the resonance frequency of the second material. In this case, corresponding to the difference (ΔF) between the resonance frequency of each material and the actual irradiation frequency, the irradiation gain and the gradient magnetic field strength are set such that the excitation region and the flip angle of each material become substantially the same, and the two-dimensional excitation is performed. As a result, when performing the two-dimensional excitation of a desired region of the object where plural materials with different resonance frequencies are present, the region is excited in a desired state where the position, shape, and flip angle of the excitation region of each material are substantially the same, without depending on the resonance frequency difference.

Second Embodiment

Next, a second embodiment of the MRI apparatus and the two-dimensional excitation adjustment method related to the present invention will be described. In the present embodiment, the irradiation frequency of the high-frequency magnetic field for two-dimensional excitation (2DRF) is set corresponding to the shape of the spectral distribution of respective materials with different resonance frequencies.

For example, due to the influence of the non-uniformity of the static magnetic field, the spectral distribution of each material may be distorted to become a broad distribution which is asymmetrical with respect to its peak position. In such a case, if the average value of the resonance frequencies of respective materials is set as the irradiation frequency of the 2DRF as in the first embodiment described above, the shape (for example, the cylinder diameter φ) and the flip angle (FA) of the two-dimensional excitation region of each material deviate from the desired state. In order to reduce such deviation, it is necessary to set the irradiation frequency of the 2DRF corresponding to the shape of the spectral distribution of each material. In the present embodiment, therefore, the irradiation frequency of the 2DRF is set corresponding to the shape of the spectral distribution of each material. Hereinafter, the present embodiment will be described in detail.

Figure 9:
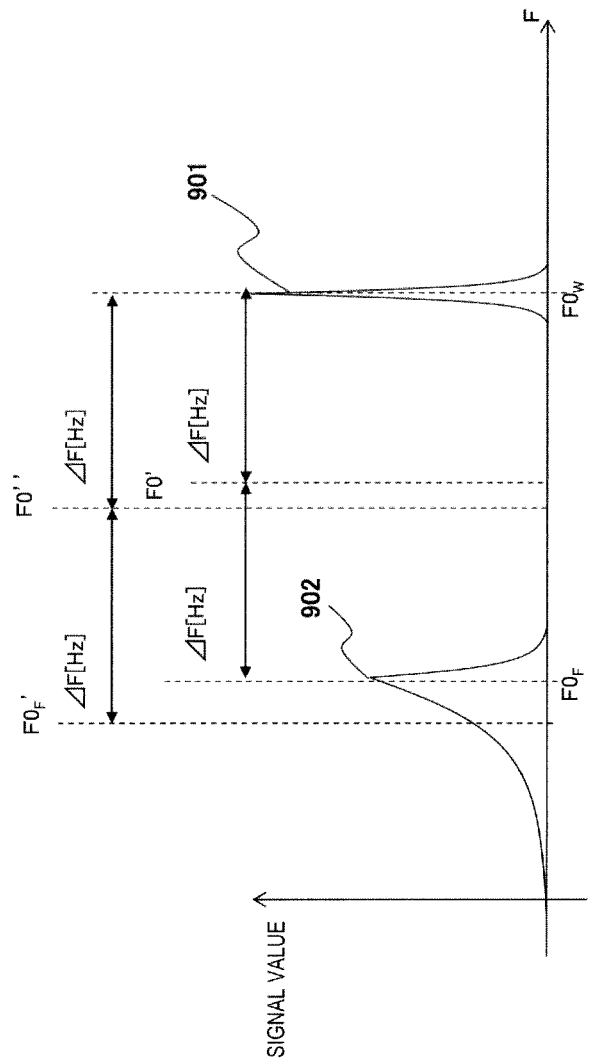
FIG. 9 is a view showing a spectral distribution of a resonance frequency in a second embodiment.

FIG. 9 shows an example of the case where the spectral distribution of each material is a broad and asymmetrical distribution. FIG. 9 shows the spectral distribution of a proton of water and the spectral distribution of a proton of fat on the same frequency axis. In particular, this is an example where the spectral distribution of the proton of fat is a broad and asymmetrical distribution. In this case, since the spectral distribution of the proton of water is approximately symmetrical with respect to its peak position, a center frequency and a peak frequency are approximately equal. On the other hand, since the spectral distribution of the proton of fat is asymmetrical with respect to its peak position, the gravity center frequency and the peak frequency are not the same.

In the present embodiment, therefore, the center frequency is calculated from the spectral distribution of each material, and an average value of the calculated center frequency of each material is set as the irradiation frequency of the 2DRF. Hereinafter, only a changed part in the process flow of the present embodiment will be described on the basis of the process flow of the first embodiment shown in FIG. 4 described above.

In step 403 in the present embodiment, the irradiation frequency setting section 340 calculates a center frequency of the spectral distribution of each material when determining the resonance frequencies $F0_W$ and $F0_F$ of the protons of water and fat and sets the center frequency as resonance frequencies $F0_W$' and $F0_F$' of the protons of water and fat. For example, the irradiation frequency setting section 340 calculates the peak frequency $F0_W$ in the spectral distribution of the proton of water and the peak frequency $F0_F$ in the spectral distribution of the proton of fat in the same manner as in the processing of step 403 in the first embodiment described first. Then, the irradiation frequency setting section 340 calculates the center of the spectrum in a range of about ±100 [Hz] with $F0_W$ and $F0_F$ as its center and sets them as $F0_W$' and $F0_F$'. Specifically, assuming that the strength of the spectrum at a frequency f is SI(f), $F0_W$' and $F0_F$' satisfy the following equation.

$$\int_{F0_W-100}^{F0_W+100} (f - F0_W') \times SI(f) df = 0 \quad (4)$$

$$\int_{F0_F-100}^{F0_F+100} (f - F0_F') \times SI(f) df = 0 \quad (5)$$

In the example shown in FIG. 9, a spectral distribution of the proton of the water of 901 is a substantially symmetrical distribution and a spectral distribution of the proton of fat of 902 is a broad asymmetrical distribution. Accordingly, $F0_W$ and $F0_W$' are substantially the same, but $F0_F$ and $F0_F$' become different values.

In step 404 in the present embodiment, the irradiation frequency setting section 340 sets an average value (F0") of F0$_W$' and F0$_F$' as an irradiation frequency of the high-frequency magnetic field (2DRF) suitable for excitation of the two-dimensional excitation region set in step 401. That is, the following Expression is satisfied.

$$F0''=(F0_W'+F0_F')/2 \qquad (6)$$

In each subsequent step, the same processing is performed by setting the difference between F0" and F0$_F$' or F0$_W$ to ΔF as shown in FIG. 9. Accordingly, detailed explanation thereof will be omitted.

As described above, according to the MRI apparatus and the two-dimensional excitation adjustment method of the present embodiment, the irradiation frequency of the 2DRF is set corresponding to the shape of the spectral distribution of each material even when the distribution of the resonance frequency of each material is a broad distribution which is asymmetrical with respect to its peak position. Therefore, even if the spectral distribution becomes a broad asymmetrical distribution due to the non-uniformity of the static magnetic field when performing the two-dimensional excitation of a desired region of the object where plural materials with different resonance frequencies are present, the region is excited in a desired state where the flip angle and the excitation region of each material are substantially the same without depending on the resonance frequency difference, similar to the effect of the first embodiment described above.

Third Embodiment

Next, a third embodiment of the MRI apparatus and the two-dimensional excitation adjustment method related to the present invention will be described. In the present embodiment, a limit value of a parameter (for example, the cylinder diameter ϕ) that specifies the shape of the two-dimensional excitation region, which is determined according to the difference (ΔF) between the resonance frequency of each material and the irradiation frequency of the high-frequency magnetic field for two-dimensional excitation, or a limit value of the flip angle of the region is calculated, and the high-frequency magnetic field adjustment is performed within the range of the calculated limit value to perform desired two-dimensional excitation. Hereinafter, the present embodiment will be described using the case where the two-dimensional cylindrical region is excited as an example, as in each embodiment described above.

Generally, a minimum diameter ϕ$_{min}$ and a maximum flip angle FA$_{MAX}$ of a cylindrical region which can be set may be calculated in advance from a maximum irradiation gain and a maximum gradient magnetic field strength which can be output from the MRI apparatus. In the first and second embodiments described above, however, the irradiation gain and the gradient magnetic field strength are determined after the difference (ΔF) between the resonance frequency of each material and the irradiation frequency of the high-frequency magnetic field for two-dimensional excitation (2DRF) is determined. For this reason, it is not possible to determine ϕ$_{min}$ and FA$_{MAX}$ in advance and perform the high-frequency magnetic field adjustment within the range of the limit value in order to perform the desired two-dimensional excitation.

Figure 10:
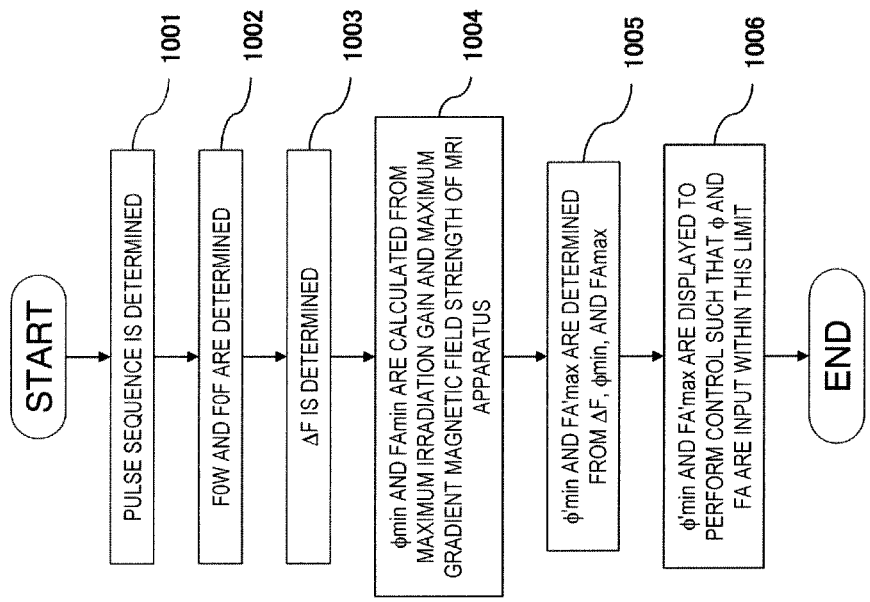
FIG. 10 is a flow chart of irradiation frequency adjustment processing of a third embodiment.

In the present embodiment, therefore, the values of ϕ$_{min}$ and FA$_{MAX}$ are acquired by calculation after determining ΔF, so that the diameter ϕ and the flip angle FA of a cylindrical region which is actually excited fall within the range of these calculated limit values. Hereinafter, the present embodiment will be described in detail on the basis of the process flow of the present embodiment shown in FIG. 10.

In step 1001, an operator selects a desired pulse sequence through a pulse sequence selection UI displayed on the display unit 111.

Figure 4:
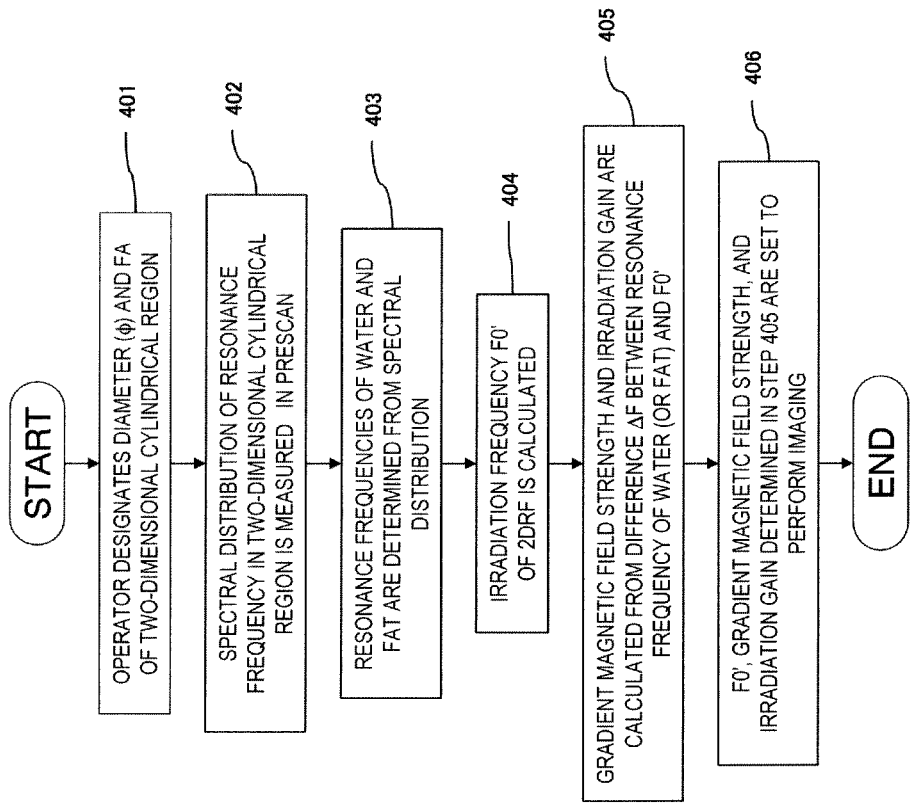
FIG. 4 is a flow chart of irradiation frequency adjustment processing of the first embodiment.

In step 1002, the irradiation frequency setting section 340 determines the resonance frequency F0$_W$ of the proton of water and the resonance frequency and F0$_F$ of the proton of fat by performing the same processing as in steps 401 to 403 in FIG. 4 described above. In addition, operator's designation of the diameter (ϕ) and the FA of the two-dimensional cylindrical region, which is equivalent to step 401, is a temporary setting for calculating each resonance frequency.

In step 1003, the irradiation frequency setting section 340 determines the difference (ΔF) between the resonance frequency F0$_W$ of the proton of water and the irradiation frequency F0' of the 2DRF by performing the same processing as in steps 404 and 405 in FIG. 4 described above.

In step 1004, the excitation region setting section 320 and the irradiation gain setting section 360 calculate the minimum diameter ϕ$_{min}$ and the maximum flip angle FA$_{MAX}$ of the cylindrical region, which can be excited, on the basis of the maximum irradiation gain and the maximum gradient magnetic field strength which can be output from the MRI apparatus.

In step 1005, the excitation region setting section 320 and the irradiation gain setting section 360 can calculate a minimum diameter ϕ'$_{min}$ and a maximum flip angle FA'$_{MAX}$ of a cylindrical region when the irradiation frequency of the 2DRF is shifted by ΔF using the following relational Expression. Then, the excitation region setting section 320 and the irradiation gain setting section 360 notify the calculation results the UI control section 350.

$$FA'_{MAX}=FA_{MAX}*FA'(\Delta F)/FA'(0) \qquad (7)$$

$$\phi'_{min}=\phi_{min}*\phi'(\Delta F)/\phi'(0) \qquad (8)$$

Here, FA'(ΔF) and ϕ'(ΔF) are functions indicating the graphs shown in FIGS. 7 and 8, respectively.

In step 1006, the UI control section 350 displays the minimum diameter ϕ'$_{min}$ and the maximum flip angle FA'$_{MAX}$ of the cylindrical region which are calculated in step 1005, on the UI screen in step 401 described above, as limit values when showing the range that can be set as an input from the operator. That is, the UI control section 350 controls an input setting of the cylinder diameter and the flip angle so that the setting input of the cylinder diameter ϕ by the operator becomes equal to or larger than ϕ'$_{min}$ and the setting input of the flip angle FA becomes equal to or smaller than FA'$_{MAX}$ in step 401 of the process flow shown in FIG. 4 in the first embodiment described above. Moreover, in the pulse sequence set in step 1001, if dB/dt or SAR exceeds the limit value when FA'$_{MAX}$ or ϕ'$_{min}$ is set, FA and ϕ not exceeding the limit value are displayed for the operator.

Thereafter, the same processing as in steps from step 402 of the process flow shown in FIG. 4 in the first embodiment described above is performed. Accordingly, detailed explanation thereof will be omitted.

The above is an explanation regarding the process flow of the present embodiment.

As described above, according to the MRI apparatus and the two-dimensional excitation adjustment method of the present embodiment, the operator can know in advance a minimum shape and the maximum flip angle of the two-dimensional excitation region, which can be set, before the setting of a shape range and the flip angle of the two-dimensional excitation region or it is not possible to set the shape range and the flip angle of the two-dimensional excitation region exceeding a range of each limit value. As a result, the operator can set the shape and the flip angle of the two-dimensional excitation region appropriately without waste.

Fourth Embodiment

Next, a fourth embodiment of the MRI apparatus and the two-dimensional excitation adjustment method related to the present invention will be described. In each of the embodiments described above, the irradiation frequency of the high-frequency magnetic field for two-dimensional excitation (2DRF), the irradiation gain, and the gradient magnetic field strength are set such that the shape and the flip angle of the excitation region of the first material are substantially the same as those of the second material. In contrast, in this embodiment, the irradiation frequency of the 2DRF, the irradiation gain, and the gradient magnetic field strength are set according to an imaging purpose such that at least one of the shape and the flip angle of the excitation region is different between the first and second materials. For example, an intermediate value (which is not an average value) of the resonance frequencies of the first and second materials is set as the irradiation frequency of the 2DRF. Hereinafter, a case where the flip angle is mainly changed between the first and second materials will be described using an IFIR method, which is a kind of an Arterial Spin Labeling (hereinafter, ASL) method of labeling the blood magnetically, as an example.

In the IFIR method, a first inversion pulse is applied to an arterial blood inflow portion in a slice-selective way and then a second inversion pulse is applied in a non-slice-selective way, so that inflow of arterial blood is forcibly longitudinally relaxed and background fabric and venous blood are inverted. An image of only the arterial blood is obtained by acquiring an echo signal after Null Time which is a period until an echo signal of water becomes substantially zero from the second inversion pulse. The details are disclosed in NPL 3.

Figure 11:
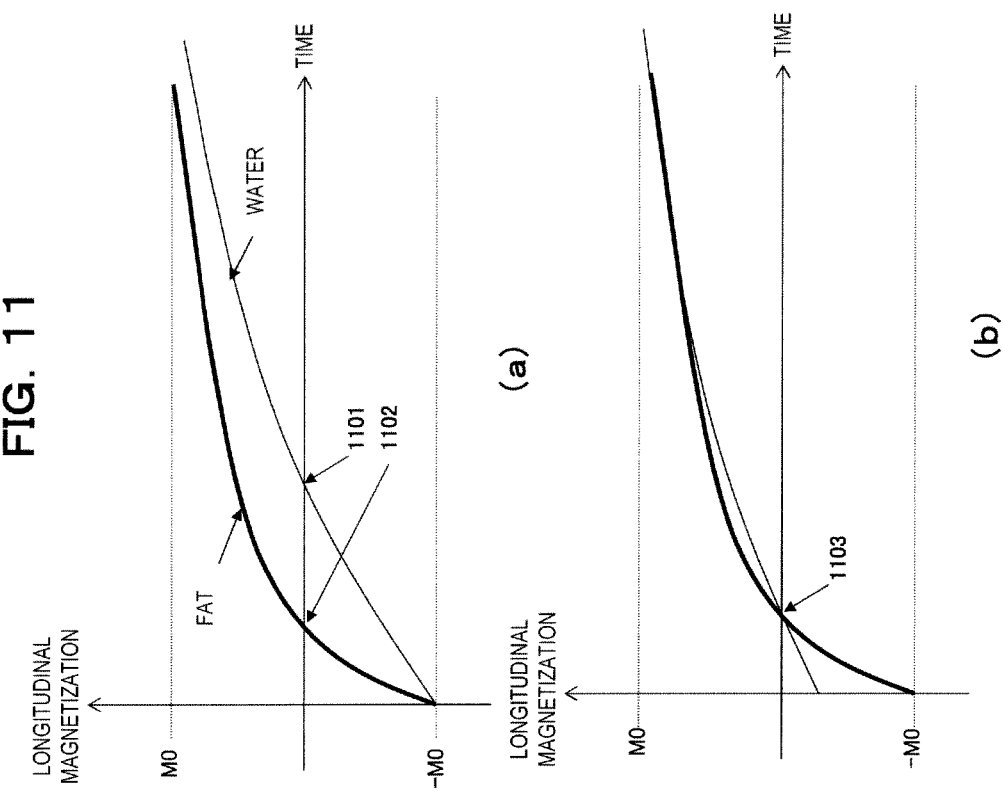
FIG. 11(a) is a view showing a recovery curve of the longitudinal magnetization of water and fat in the related art.
FIG. 11(b) is a view showing a recovery curve of the longitudinal magnetization of water and fat in a fourth embodiment.

FIG. 11 shows a state of a temporal change where longitudinal magnetization of each of water and fat is longitudinally relaxed immediately after being reversed. FIG. 11(a) shows each state of relaxation of the longitudinal magnetization when water and fat are excited at the same angle. FIG. 11(b) shows each state of relaxation of the longitudinal magnetization when water and fat are excited at different angles in the present embodiment. Since T1, which is a time constant of the longitudinal relaxation, of fat is smaller than T1 of water, relaxation of the longitudinal magnetization of fat is earlier than relaxation of the longitudinal magnetization of water. For this reason, the size of the longitudinal magnetization becomes zero by the longitudinal relaxation. As a result, the Null Time at which a detected echo signal becomes substantially zero in fat becomes earlier than that in water. In addition, at the Null Time of water, the longitudinal magnetization of fat is greatly recovered to detect echo signals from fat. In the IFIR method, an echo signal is measured at a Null Time 1101 of a water signal, as shown in FIG. 11(a). Accordingly, since a fat signal is not suppressed (FIG. 11(a)), it is necessary to apply a fat suppression pulse in advance of the second inversion pulse.

In the present embodiment, therefore, as shown in FIG. 11(b), a flip angle $FA_W$ of water and a flip angle $FA_F$ of fat are changed to set $FA_W$ of water and $FA_F$ of fat, at which the Null Time of water and the Null Time of fat become the same 1103, as optimal flip angles, and the second inversion pulse for these flip angles of water and fat is used. In addition, it is not necessary to change the flip angle of the first inversion pulse. In this case, although the cylinder diameter φ of water is also different from the cylinder diameter φ of fat, it is necessary to make both the cylinder diameters sufficiently large for a field of view (FOV). When φ is sufficiently large for the FOV, a plateau portion of an excitation profile (flat portion of the excitation profile) of the 2DRF is applied to the FOV. Accordingly, since the difference between the cylinder diameter φ of water and the cylinder diameter φ of fat can be neglected, it can be treated as a non-selection IR pulse. Preferably, since the Null Time of fat is 160 to 180 [ms] when $FA_F$ of fat is set to 180 [deg], FA of water at which the Null Time of water is 160 to 180 [ms] is set as an optimal $FA_W$. In this case, since echo signals of water and fat are suppressed simultaneously, it is not necessary to apply a fat suppression pulse additionally. This shortens the imaging time.

Figure 12:
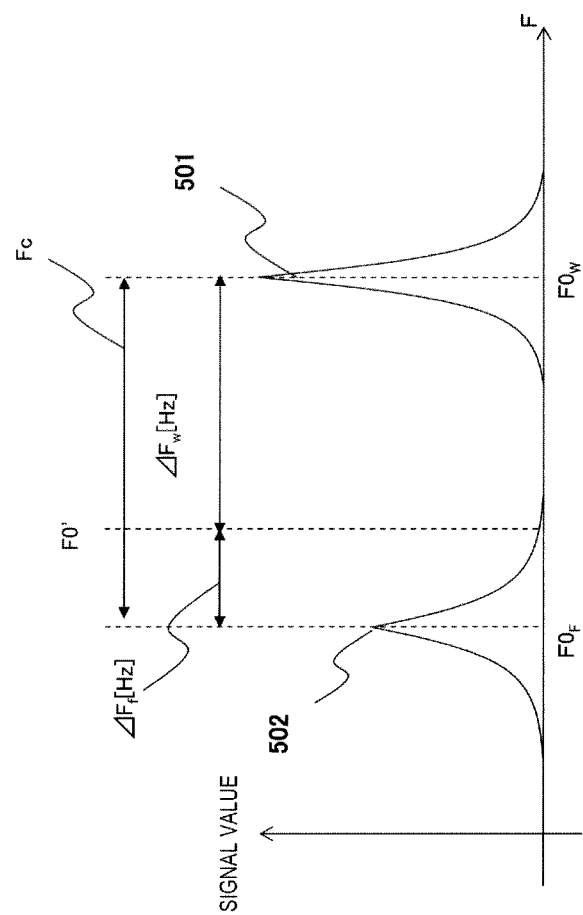
FIG. 12 is a view showing the relationship between a spectral distribution of a resonance frequency and an irradiation frequency of a 2DRF in the fourth embodiment.
Figure 13:
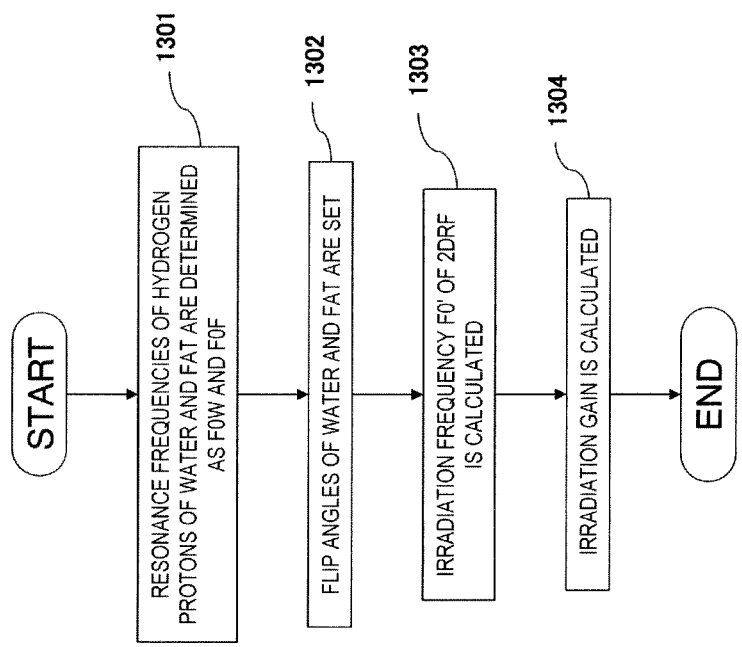
FIG. 13 is a flow chart of irradiation frequency adjustment processing of the fourth embodiment.

When the flip angles of water and fat are set differently according to the imaging purpose, a target ratio of $FA_W$ of water to $FA_F$ of fat is first calculated, and the irradiation frequency F0' of the 2DRF is calculated from the function FA' (ΔF) determined by a high-frequency magnetic field waveform. Hereinafter, a method of calculating the irradiation frequency F0' of the 2DRF which is performed by the irradiation frequency setting section 340 in the present embodiment will be described using the relationship between the spectral distribution of the resonance frequency and the irradiation frequency F0' of the 2DRF shown in FIG. 12 and the process flow shown in FIG. 13.

In step 1301, the resonance frequencies of the protons of water and fat are determined as $F0_W$ and $F0_F$, respectively, in the same manner as in the first or second embodiment described above. That is, steps 401 to 403 in the process flow of the first embodiment shown in FIG. 4 are performed to determine the resonance frequencies $F0_W$ and $F0_F$ of the protons of water and fat. In this case, an echo signal acquired by performing a prescan of the entire FOV is used without designating a cylindrical region. The irradiation gain setting section 360 sets a difference between the resonance frequencies $F0_W$ and $F0_F$ as $F_C$ by the following Expression.

$$F_C = F0_W - F0_F \tag{9}$$

In step 1302, the irradiation gain setting section 360 sets the flip angles of water and fat. For example, the flip angle of water is set to be smaller than that of fat such that the Null Time of water matches that of fat, in the same manner as in the IFIR method described above. In addition, target flip angles of water and fat may be input by the operator through the UI screen displayed by the UI control section 350 or may be stored in the MRI apparatus.

Assuming that the target flip angle of fat is $FA_F$ and the target flip angle of water is $FA_W$, a ratio of the flip angle of water to the flip angle of fat is set as β by the following Expression (10).

$$\beta = FA_W / FA_F \tag{10}$$

In step 1303, the irradiation gain setting section 360 calculates the irradiation frequency F0' of the 2DRF which realizes Expression (10). Specifically, this is as follows. That is, the flip angles $FA_W$ and $FA_F$ of water and fat can be calculated from the function FA'(ΔF) using the following Expressions.

$$FA_W = FA'(\Delta F_W)$$

$$FA_F = FA'(\Delta F_F)$$

By substituting the above Expressions into Expression (10), Expression (10A) is obtained.

$$\beta = FA'(\Delta F_W) / FA'(\Delta F_F) \tag{10A}$$

Here, differences between the irradiation frequency F0' of the 2DRF and the resonance frequencies of the protons of water and fat are assumed to be $\Delta F_W$ and $\Delta F_F$, respectively. Specifically, $\Delta F_W$ and $\Delta F_F$ are defined by Expression (11).

$$\Delta F_W = F0_W - F0' \quad (11\text{-}1)$$

$$\Delta F_F = F0' - F0_F \quad (11\text{-}2)$$

Accordingly, $\Delta F_W$ and $\Delta F_F$ satisfy the following relationship.

$$\Delta F_W + \Delta F_F = F_C \quad (12)$$

By substituting Expression (12) into Expression (10A), (10B) is obtained as Expression of $\Delta F_F$.

$$\beta = FA'(F_C - \Delta F_F)/FA'(\Delta F_F) \quad (10B)$$

When there is plural solutions of the function (10B), the irradiation frequency F0' of the 2DRF is calculated from Expression (11-2) using a minimum value of positive values as $\Delta F_F$. In this case, the irradiation frequency F0' is not an average value but an intermediate value of the resonance frequencies F0$_W$ and F0$_F$ of the protons of water and fat. In the example shown in FIG. 12, the irradiation frequency F0' is an intermediate value close to fat. In addition, since $\Delta F$ is minimized, the irradiation gain $T_W$ can be minimized as a result.

In addition, there may be no solution of (10B) by $\beta$ or the function FA'($\Delta F$). This is because the function FA'($\Delta F$) is determined by the high-frequency magnetic field waveform, but the minimum value of FA'($\Delta F$) is FA'(0)/2 regardless of the high-frequency magnetic field waveform. That is, this is because a minimum value of $\beta$ becomes ½ and accordingly a range of $\beta$ is limited. When there is no solution, the irradiation frequency setting section 340 notifies it to the UI control section 350. The UI control section 350 may show the operator a suggestion that there is no setting value of the flip angle, or a $\beta$ value or the like whose solution is obtained may be set as a limit value of a value, which can be set by the operator, in the stage where $\Delta F_W$ and $\Delta F_F$ are determined.

In step 1304, the irradiation gain setting section 360 calculates the irradiation gain $T_W$ in the same manner as in step 405 of the first embodiment under the conditions of FA'=FA' ($\Delta F_F$). As a result, the target flip angle FA' can be realized.

The above is an explanation regarding the process flow of the method of calculating the irradiation frequency F0' of the 2DRF which is performed by the irradiation frequency setting section 340. Target imaging is performed using the irradiation frequency F0' of the 2DRF calculated in this way.

As described above, according to the MRI apparatus and the two-dimensional excitation adjustment method of the present embodiment, at least one of the cylinder diameter $\phi$ and the flip angle FA is set to be different between the regions of the first and second materials according to the imaging purpose. Therefore, it becomes possible to acquire an image fit for the desired imaging purpose.

Fifth Embodiment

Next, a fifth embodiment of the MRI apparatus and the two-dimensional excitation adjustment method related to the present invention will be described. In the present embodiment, when the resonance frequencies of the first and the second materials included in the object placed in the non-uniform static magnetic field space are shifted due to the non-uniformity of the static magnetic field, the irradiation frequency of the high-frequency magnetic field for two-dimensional excitation (2DRF) is set corresponding to the non-uniformity of the static magnetic field.

Within an imaging surface, there is spatial non-uniformity of the static magnetic field. Within the imaging surface, the resonance frequency of a material to be imaged is distributed in a range of about tens of Hertz to 100 [Hz] due to the non-uniformity of the static magnetic field. For this reason, when the spectral distribution of the resonance frequency in the first to fourth embodiments described above is acquired from the entire imaging surface, it becomes a spectral distribution including a dispersion of the resonance frequency. As a result, the irradiation frequency of the 2DRF determined from the spectral distribution may be different from the resonance frequency of the desired two-dimensional excitation region.

In the present embodiment, therefore, a region for acquisition of the spectral distribution is limited to a local region where the static magnetic field can be regarded as substantially fixed, so that there is no influence of the non-uniformity of the static magnetic field. For example, when the cylindrical region shown in FIG. 5 is excited as the two-dimensional excitation region, a local region 1402, which is a portion in a cylindrical region 1401 to be excited, is excited and the spectral distribution is acquired using echo signals from the local region 1402, as shown in FIG. 14.

First, the setting of the local region 1402 will be described on the basis of FIG. 14. The positioning image 510 acquired in advance is displayed on the UI screen 500. On this positioning image 510, the operator sets the two-dimensional excitation region 1401 and the local region 1402. Here, the two-dimensional excitation region 1401 is a cylindrical region excited by the SS method, and the local region 1402 is a region, which is focused in particular, of the two-dimensional excitation region. Here, as an example, the local region 1402 is made to have a cylindrical shape with the same axis as the two-dimensional excitation region 1401 and the same radius of the cross section.

In addition, any input of the two-dimensional excitation region 1401 and the local region 1402 may be received first. For example, in the case of receiving the two-dimensional excitation region 1401 first, the two-dimensional excitation region 1401 may be set by arbitrary position and angle as indicated by an arrow in the drawing. Then, the local region 1402 may slide in the axial direction of a cylinder within a region along the cylinder set as the two-dimensional excitation region 1401 as indicated by an arrow in the drawing. In the case of receiving the local region 1402 first, the two-dimensional excitation region 1401 is received as a cylinder with the same axis as the set local region 1402.

Figure 14:
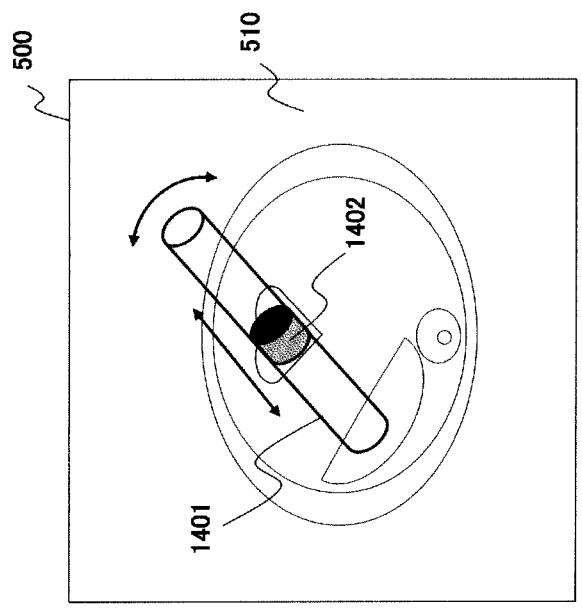
FIG. 14 is an explanatory view of a UI screen of a fifth embodiment.

In addition, although both the two-dimensional excitation region 1401 and the local region 1402 are formed as cylinders (columnar shapes) and their cross-sectional shapes are circles in FIG. 14, the two-dimensional excitation region 1401 and the local region 1402 are not limited to having these shapes. These cross-sectional shapes may be set arbitrarily.

Next, a method of collecting echo signals from the local region 1402 will be described.

Figure 15:
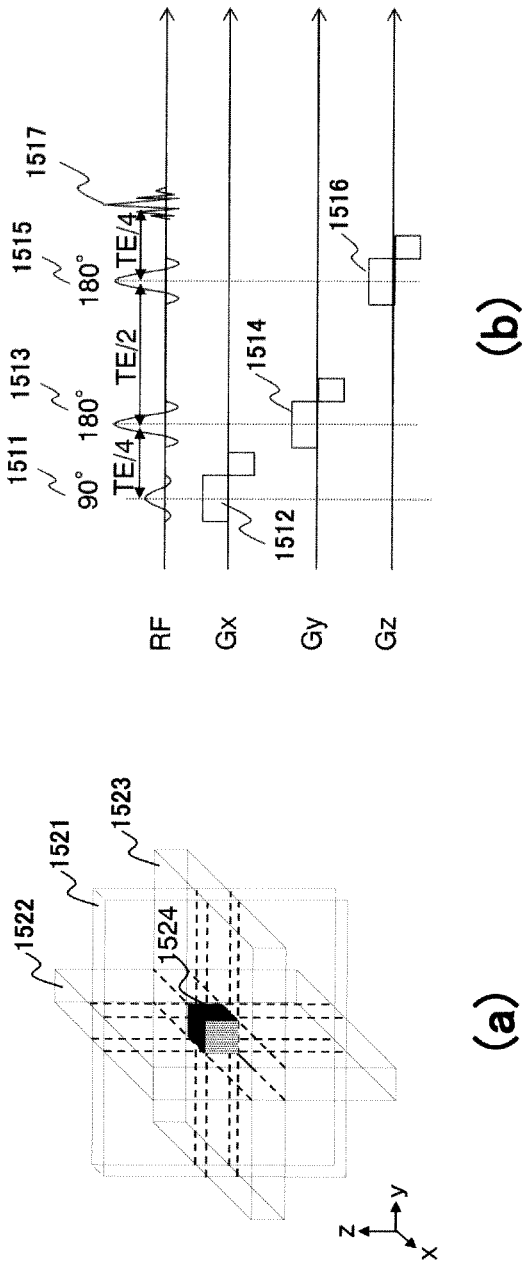
FIG. 15(a) is an explanatory view of a region excited by an orthogonal three cross-section excitation method of the fifth embodiment.
FIG. 15(b) is a pulse sequence diagram of the orthogonal cross-section excitation method.

As a first method of collecting echo signals from the local region 1402, an orthogonal three cross-section excitation method is used. On the basis of FIG. 15, the orthogonal three cross-section excitation method will be described in detail. FIG. 15(a) shows a local region which is a common portion where orthogonal three cross sections cross each other and which is excited, and FIG. 15(b) shows a pulse sequence used in the orthogonal three cross-section excitation method. In the orthogonal three cross-section excitation method, a region (intersection region) 1524 of a rectangular parallelepiped in which the orthogonal three cross sections cross each other is excited. Here, the intersection region 1524 is excited so that the cylindrical local region 1402 is inscribed. In order to excite such a region, with the resonance frequency measured in advance as the irradiation frequency F0, a first gradient magnetic field 1512 is applied in the x-axis direction (Gx) together with a 90° pulse 1511 so that a predetermined cross section (first cross section) 1521 is excited in the x-axis direction as shown in FIG. 15 (b). After echo time (TE)/4 from the application of the 90° pulse 1511, a second gradient magnetic field 1514 is applied in the y-axis direction (Gy) together with a first 180° pulse 1513, and nuclear magnetization of a region where the first cross section 1521 and a cross section (second cross section) 1522 in the y-axis direction specified by this cross each other is excited. After time TE/2 from the application of the first 180° pulse 1513, a third gradient magnetic field 1516 is applied in the z-axis direction (Gz) together with a second 180° pulse 1515, and nuclear magnetization of the region 1524 where the first and second cross sections 1521 and 1522 and a cross section (third cross section) 1523 in the z-axis direction specified by this cross each other is excited. Then, an echo signal 1517 generated at the timing of time TE/4 after the application of the second 180° pulse 1515 is collected. Moreover, in the pulse sequence described above, the order of application axes for the application of gradient magnetic fields does not matter.

Figure 16:
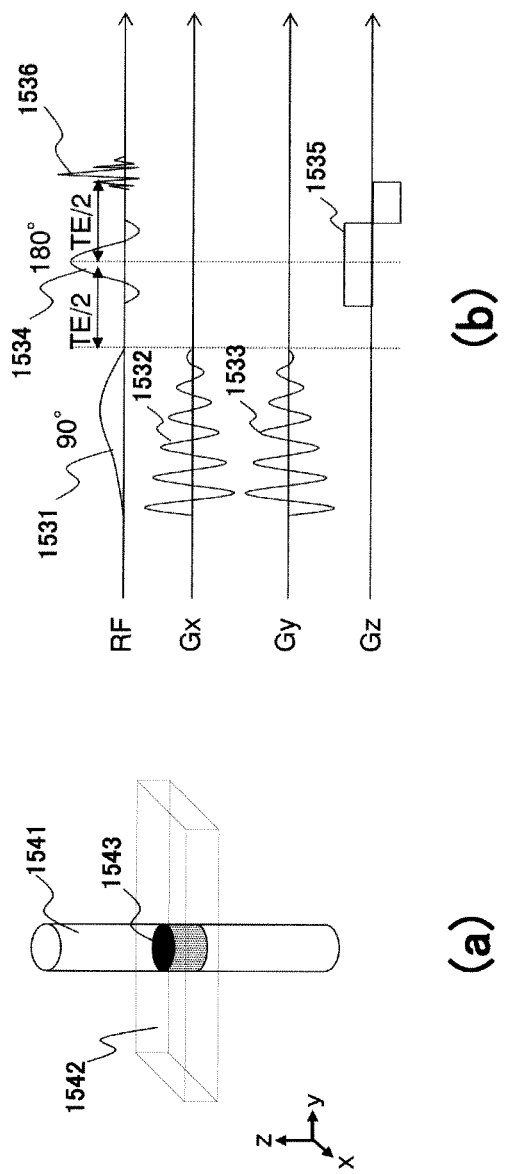
FIG. 16(a) is an explanatory view of a region excited by a 2D orthogonal 1D method of the fifth embodiment.
FIG. 16(b) is a pulse sequence diagram of the 2D orthogonal 1D method.

As a second method of collecting echo signals from the local region 1402, a two-dimensional excitation method is used. On the basis of FIG. 16, the two-dimensional excitation method will be described in detail. Regarding the two-dimensional excitation method, FIG. 16 is a view for explaining an excitation region and a pulse sequence when the two-dimensional excitation and excitation of one cross section, which is perpendicular to an axis of a cylindrical region excited by the two-dimensional excitation, are combined with each other (2D orthogonal 1D method). FIG. 16(a) is a view for explaining the region excited by the 2D orthogonal 1D method, and FIG. 16(b) is a pulse sequence diagram of the 2D orthogonal 1D method. In addition, in FIG. 16(a), each cross section and the cylindrical region are transparently shown for the sake of explanation.

In the 2D orthogonal 1D method, first, a first oscillating gradient magnetic field 1532 is applied in the x-axis direction (Gx) and a second oscillating gradient magnetic field 1533 is applied in the y-axis direction (Gy) together with a 90° pulse (2DRF) 1531, so that a cylindrical region 1541 is excited. After time TE/2 from the application of the 90° pulse (2DRF) 1531, a gradient magnetic field 1535 is applied in the z-axis direction (Gz) together with a 180° pulse 1534 so that a phase of nuclear magnetization of an intersection region 1543 between a cross section 1542 and the cylindrical region 1541 is returned. Then, an echo signal 1536 generated at the timing of time TE/2 after the application of the 180° pulse 1534 is collected. Processing on the obtained echo signal 1536 and the method of calculating the irradiation frequency F0' of the 2DRF are the same as in each embodiment described above.

Here, the imaging parameter is set such that the intersection region 1543 matches the local region 1402. In addition, the irradiation frequency used for the 90° pulse 1531 of the pulse sequence described above is the overall irradiation frequency F0 determined in advance by the conventional method.

Figure 17:
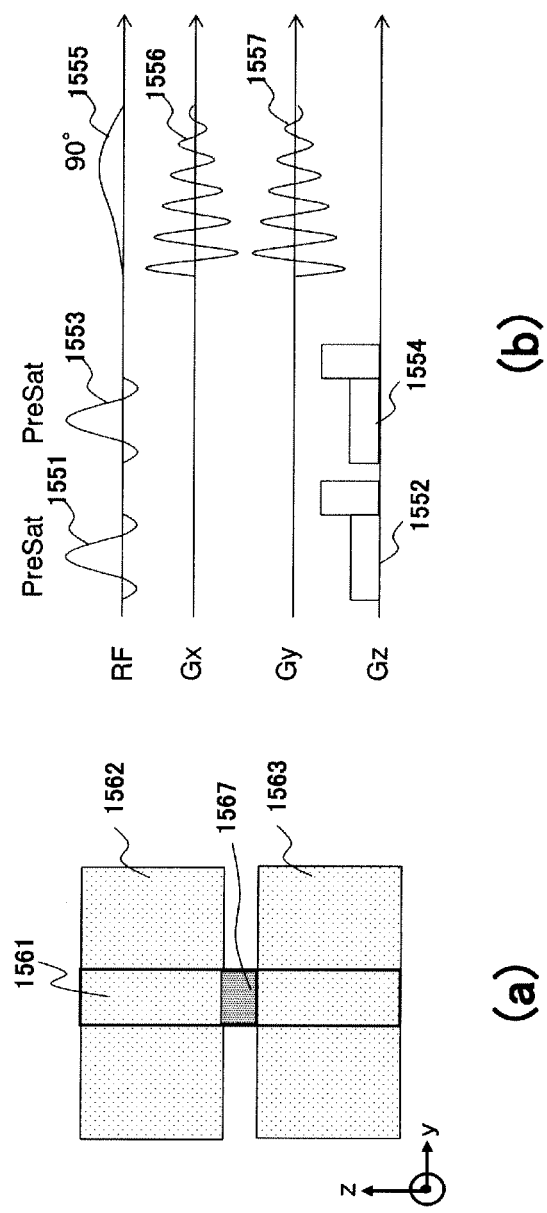
FIG. 17(a) is an explanatory view of a region excited by a 2D pre-saturation method of the fifth embodiment.
FIG. 17(b) is a pulse sequence diagram of the 2D pre-saturation method.

As a third method of collecting echo signals from the local region 1402, a pre-saturation method is used. The pre-saturation method will be described in detail using FIG. 17. In the pre-saturation method, the two-dimensional excitation and a pre-saturation pulse are combined to suppress an echo signal from a region other than the local region 1402 in the cylindrical region excited by the two-dimensional excitation. FIG. 17(a) is a view for explaining a region excited by a 2D pre-saturation method, and is a view seen from the x-axis direction. FIG. 17(b) is a pulse sequence diagram of the 2D pre-saturation method.

In the 2D pre-saturation method, first, a first gradient magnetic field 1552 is applied in the z-axis direction (Gz) together with a first pre-saturation pulse 1551 in order to demagnetize a first region 1562. In addition, a second gradient magnetic field 1554 is applied in the z-axis direction (Gz) together with a second pre-saturation pulse 1553 in order to demagnetize a second region 1563. Any of the first and second regions 1562 and 1563 may be demagnetized first. Then, a first oscillating gradient magnetic field 1556 is applied in the x-axis direction (Gx) and a second oscillating gradient magnetic field 1557 is applied in the y-axis direction (Gy) together with a 90° pulse (2DRF) 1555, so that a region (non-intersection region) 1567 other than the first and second regions 1562 and 1563 in a cylindrical region 1561 is excited. Then, an echo signal generated at the timing of time TE after the application of the 90° pulse (2DRF) 1555 is collected. Processing on the obtained echo signal and the method of calculating the irradiation frequency F0' of the 2DRF are the same as in each embodiment described above.

Here, the imaging parameter is set such that the non-intersection region 1567 matches the local region 1402. In addition, the irradiation frequency used for the 90° pulse 1555 of the pulse sequence described above is the overall irradiation frequency F0 determined in advance by the conventional method.

Until now, the method of collecting echo signals from a local region has been described. The signal collection section 330 collects echo signals without encoding by executing any of the methods described above. Then, a Fourier transform of the collected signals is performed in a time direction. As a result of the Fourier transform, a spectral distribution in the local region 1402 is obtained. Thereafter, the same processing as in each of the embodiments described above is performed to calculate the irradiation frequency F0' for 2DRF, the irradiation gain $T_W'$, and the gradient magnetic field strength $G_W'$.

As described above, according to the MRI apparatus and the two-dimensional excitation adjustment method of the present embodiment, the spectral distribution is acquired from the local region where the static magnetic field can be regarded as substantially fixed, so that there is no influence of the non-uniformity of the static magnetic field. Accordingly, even if the resonance frequency is shifted due to the non-uniformity of the static magnetic field, the irradiation frequency of the 2DRF can be appropriately set corresponding to the non-uniformity of the static magnetic field. As a result, it is possible to set correctly the position and shape of the excitation region of the first and second materials and its flip angle.

Sixth Embodiment

Next, a sixth embodiment of the MRI apparatus and the two-dimensional excitation adjustment method related to the present invention will be described. In the fifth embodiment described above, in order to eliminate the dispersion of the spectral distribution due to the non-uniformity of the static magnetic field, the spectral distribution of the local region is acquired and the irradiation frequency of the high-frequency magnetic field for two-dimensional excitation (2DRF) is calculated corresponding to the static magnetic field strength of the local region. On the other hand, in the present embodiment, the non-uniformity of the static magnetic field of the local region is corrected by adjusting the static magnetic field such that the resonance frequency of nuclear magnetization of the region matches the overall irradiation frequency F0 acquired in advance. Hereinafter, a method of correcting the non-uniform static magnetic field distribution of the local region in the present embodiment will be described in detail.

Figure 18:
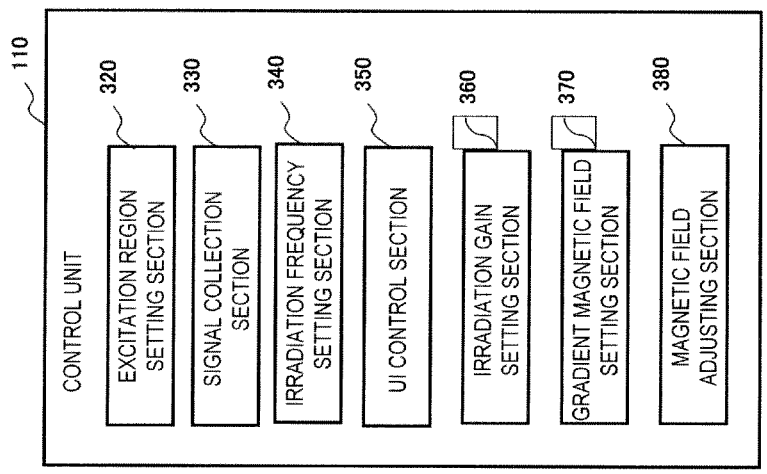
FIG. 18 is a functional block diagram of a control unit of a sixth embodiment.

FIG. 18 is a functional block diagram of the control unit 110 of the present embodiment. In the present embodiment, in order to realize the functions of the present embodiment, a magnetic field adjusting section 380 which adjusts a magnetic field of the local region is further provided. Hereinafter, magnetic field adjustment processing of the magnetic field adjusting section 380 in the present embodiment, which is different from the fifth embodiment, will be described. Other configurations and processing are the same as those in the fifth embodiment.

The magnetic field adjusting section 380 of the present embodiment reduces the non-uniformity of the static magnetic field of a local region in order to make the resonance frequency of nuclear magnetization in the local region 1402 match the overall resonance frequency F0. Specifically, a shim current value Is for correcting the non-uniformity of the static magnetic field of the local region 1402 is calculated from volume data or a shim image, which is acquired by the signal collection section 330 using the same method as in the fifth embodiment, using the conventional method. In addition, the shim current is calculated only for an axis on which the current value can be changed during measurement (scan). In addition, the magnetic field adjusting section 380 controls a shim power source such that a value of a current applied to a shim coil in the axial direction is set as the calculated Is only during 2DRF application.

The magnetic field adjustment processing of the magnetic field adjusting section 380 will be described using FIGS. 19 and 20. In the magnetic field adjustment processing of the present embodiment, the shim current value Is for making a static magnetic field strength B1 in the local region 1402 become a static magnetic field strength B0, which realizes the overall frequency F0, is calculated. Here, a case will be described in which the local region 1402 has a cylindrical shape and the axial direction matches the z-axis direction of the inspection space. In addition, it is assumed that a static magnetic field strength component can be corrected up to a first-order component in each axial direction of the shim coil. That is, a current value for making the overall irradiation frequency F0 match the resonance frequency F calculated from a zero-order component of the static magnetic field strength B1 is calculated.

Figure 19:
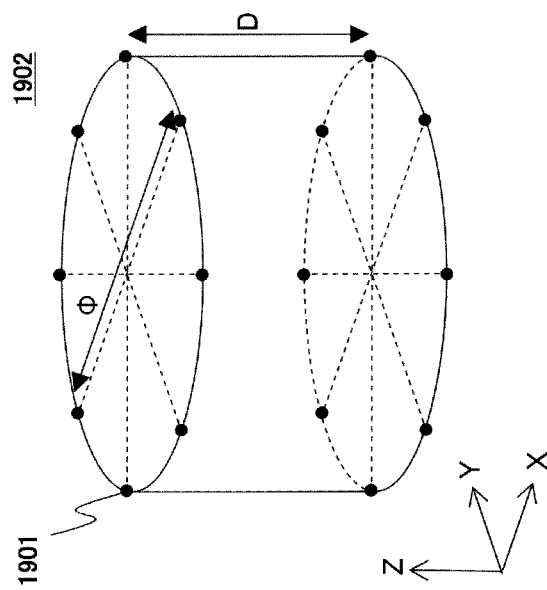
FIG. 19 is an explanatory view of an imaging result of a local selection region of the sixth embodiment.

FIG. 19 is an imaging result of the local region 1402. Plural measurement points 1901 are set on the circumference of upper and lower surfaces of the cylindrical local region 1402 with a diameter φ and a thickness D. In addition, it is preferable that the plural measurement points 1901 be placed symmetrically with respect to the axis of this cylinder. Preferably, the measurement points 1901 are placed isotropically in the sectional direction of the axis.

Figure 20:
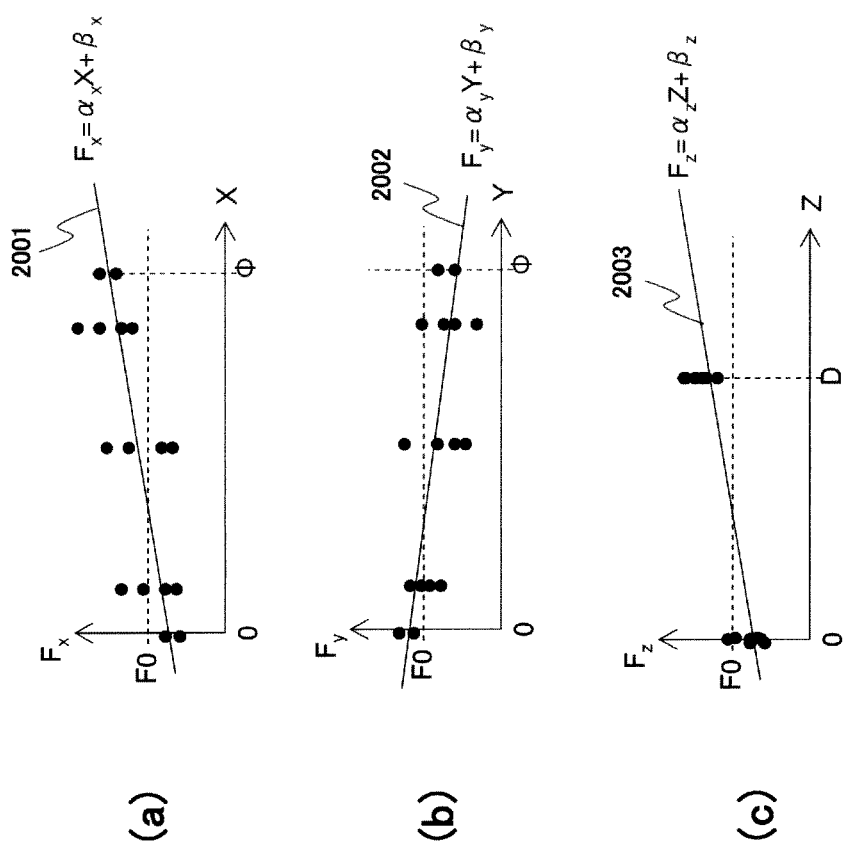
FIGS. 20(a) to 20(c) are explanatory views of a result of projection of a resonance frequency in each axial direction in the sixth embodiment.

A result obtained by projecting the resonance frequency F, which is calculated from the static magnetic field strength B1 of each measurement point 1901, in each direction of the x, y, and z axes (Fx, Fy, Fz) and plotting is shown in FIG. 20. In addition, FIG. 20(a) is a result when the resonance frequency F is projected in the x-axis direction, FIG. 20(b) is a result when the resonance frequency F is projected in the y-axis direction, and FIG. 20(c) is a result when the resonance frequency F is projected in the z-axis direction. In each drawing, the horizontal axis is a position in each axial direction, and the vertical axis is the resonance frequency F calculated from the static magnetic field strength B1.

The projection result in each axial direction approximates the first-order equation. Here, it is assumed that an approximate equation 2001 of the projection result in the x-axis direction is $F_x=\alpha_x x+\beta_x$, an approximate equation 2002 of the projection result in the y-axis direction is $F_y=\alpha_y y+\beta_y$, and an approximate equation 2003 of the projection result in the z-axis direction is $F_z=\alpha_z z+\beta_z$. The shim current value is determined such that all of them pass through F0 and their inclinations become 0. That is, the shim current value Is is a value which realizes the gradient magnetic field strength in which the approximate equations of an x-axis component, a y-axis component, and a z-axis component of the calculated resonance frequency F' become $F'_x=-\alpha_x x-\beta_x+F0$, $F'_y=-\alpha_y y-\beta_y+F0$, and $F'_z=-\alpha_z x-\beta_x+F0$, respectively.

In the present embodiment, imaging is performed by applying the shim current value Is, which is calculated by the magnetic field adjusting section 380, only during 2DRF application in the method described above. Other than that, imaging is performed by applying the shim current value Is of or applying the shim current value which reduces the non-uniformity of the static magnetic field of the entire imaging region. As a result, according to the present embodiment, a desired excitation profile for the 2DRF can be acquired even if the static magnetic field is not uniform in the local region 1402.

In addition, the correction order of the non-uniformity of the static magnetic field using the shim coil is not limited to the above. A projection result of each measurement point 1901 in each axial direction of the static magnetic field strength B1 can be made to approximate in a range of the order in which the shim coil in the corresponding axial direction can correct the static magnetic field strength. In addition, the method of calculating the shim current value for achieving the uniformity of the static magnetic field is not limited to the method described above. Various kinds of general methods may be used.

In addition, when the order in which the non-uniformity of the static magnetic field is to be corrected is a first order, it is possible to correct the non-uniformity of the static magnetic field using a gradient magnetic field based on the gradient magnetic field coil 103. That is, control is performed such that the same amount of current as the shim current value Is calculated by the above-described method is supplied from the gradient magnetic field power source 106 to each gradient magnetic field coil 103 as an offset only during 2DRF application. By correcting the non-uniformity of the static magnetic field using the gradient magnetic field coil 103, the non-uniformity of the static magnetic field of the local region 1402 can be corrected during 2DRF application even if the MRI apparatus 100 does not include the shim coil.

Since processing of measuring an echo signal from the local region 1402 in a state where the non-uniformity of the static magnetic field of the local region 1402 is corrected for adjustment to predetermined static magnetic field strength, calculating the spectral distribution from the measured echo signal, and determining the irradiation frequency F0' for 2DRF, the irradiation gain $T_W'$, and the gradient magnetic field strength $G_W'$ on the basis of the calculated spectral distribution is the same as in the fifth embodiment described above, detailed explanation thereof will be omitted.

As described above, according to the MRI apparatus and the two-dimensional excitation adjustment method of the present embodiment, the non-uniformity of the static magnetic field of the local region is corrected such that the resonance frequency of nuclear magnetization of the local selection region matches the overall irradiation frequency F0 acquired in advance. Therefore, it is possible to set correctly the position and shape of the excitation region of the first and second materials and its flip angle without broadening of the spectral distribution acquired from the local selection region.

DESCRIPTION OF REFERENCE NUMERALS AND SIGNS

- 100: MRI apparatus
- 101: object
- 102: magnet
- 103: gradient magnetic field coil
- 104: RF coil
- 105: RF probe
- 106: gradient magnetic field power source
- 107: RF transmission unit
- 108: signal detection unit
- 109: signal processing unit
- 110: control unit
- 111: display unit
- 112: operation unit
- 113: bed
- 201: RF
- 202: gradient magnetic field
- 211: RF
- 212: oscillating gradient magnetic field
- 213: oscillating gradient magnetic field
- 320: excitation region setting section
- 330: signal collection section
- 340: irradiation frequency setting section
- 350: UI control section
- 360: irradiation gain setting section
- 370: gradient magnetic field setting section
- 380: magnetic field adjusting section

The invention claimed is:

1. A magnetic resonance imaging apparatus comprising:
a control unit that controls measurement of an echo signal, which is generated from a two-dimensional excitation region of an object placed in a static magnetic field, using a pulse sequence with a high-frequency magnetic field and a gradient magnetic field for performing two-dimensional excitation of the two-dimensional excitation region of the object,
wherein the object is formed by a first material with a first resonance frequency and a second material with a second resonance frequency, and
the control unit includes an irradiation frequency setting section which sets an irradiation frequency of the high-frequency magnetic field on the basis of imaging conditions related to the two-dimensional excitation and the first and second resonance frequencies so that desired regions of the first and second materials are excited in a two-dimensional manner,
wherein the control unit includes an irradiation gain setting section which sets an irradiation gain of the high-frequency magnetic field on the basis of an excitation angle of the two-dimensional excitation region and a frequency difference between the irradiation frequency and the first resonance frequency.

2. The magnetic resonance imaging apparatus according to claim 1,
wherein the irradiation gain setting section sets the irradiation gain of the high-frequency magnetic field on the basis of a function or data showing a relationship between the excitation angle and the frequency difference between the irradiation frequency and the first resonance frequency.

3. The magnetic resonance imaging apparatus according to claim 2,
wherein the irradiation gain setting section calculates a maximum value, which can be set, of the excitation angle of the two-dimensional excitation region on the basis of a predetermined maximum value of the excitation angle of the two-dimensional excitation region and the frequency difference between the irradiation frequency and the first resonance frequency, and
a display unit that displays the maximum value is provided.

4. The magnetic resonance imaging apparatus according to claim 1,
wherein the control unit includes a gradient magnetic field setting section which sets a strength of the gradient magnetic field on the basis of a value of a parameter indicating a shape of the two-dimensional excitation region and a frequency difference between the irradiation frequency and the first resonance frequency.

5. The magnetic resonance imaging apparatus according to claim 4,
wherein the gradient magnetic field setting section sets the strength of the gradient magnetic field on the basis of a function or data showing a relationship between the value of the parameter indicating the shape of the two-dimensional excitation region and the frequency difference between the irradiation frequency and the first resonance frequency.

6. The magnetic resonance imaging apparatus according to claim 4,
wherein the control unit includes an excitation region setting section which sets the value of the parameter indicating the shape of the two-dimensional excitation region according to an input for setting the two-dimensional excitation region.

7. The magnetic resonance imaging apparatus according to claim 6,
wherein the excitation region setting section calculates a minimum value, which can be set, of the value of the parameter indicating the shape of the two-dimensional excitation region on the basis of a predetermined minimum value of the value of the parameter indicating the shape of the two-dimensional excitation region and the frequency difference between the irradiation frequency and the first resonance frequency, and
a display unit that displays the minimum value is provided.

8. The magnetic resonance imaging apparatus according to claim 1,
wherein the irradiation frequency setting section sets an average value of the first and second resonance frequencies as the irradiation frequency.

9. The magnetic resonance imaging apparatus according to claim 1,
wherein the irradiation frequency setting section sets an intermediate value of the first and second resonance frequencies as the irradiation frequency such that an excitation angle of the first material is different from an excitation angle of the second material.

10. A magnetic resonance imaging apparatus comprising:
a control unit that controls measurement of an echo signal, which is generated from a two-dimensional excitation region of an object placed in a static magnetic field, using a pulse sequence with a high-frequency magnetic field and a gradient magnetic field for performing two-dimensional excitation of the two-dimensional excitation region of the object, wherein the object is formed by a first material with a first resonance frequency and a second material with a second resonance frequency, and the control unit includes an irradiation frequency setting section which sets an irradiation frequency of the high-frequency magnetic field on the basis of imaging conditions related to the two-dimensional excitation and the first and second resonance frequencies so that desired regions of the first and second materials are excited in a two-dimensional manner, wherein the control unit includes a signal collection section which acquires an echo signal from the two-dimensional excitation region using a high-frequency magnetic field with an initial irradiation frequency determined in advance, and the irradiation frequency setting section determines the first and second resonance frequencies on the basis of the echo signal acquired from the two-dimensional excitation region using the high-frequency magnetic field with the initial irradiation frequency.

11. The magnetic resonance imaging apparatus according to claim 10, wherein the irradiation frequency setting section determines the first and second resonance frequencies on the basis of a spectral distribution of the resonance frequency of each material, which is obtained by a Fourier transform of the echo signal acquired from the two-dimensional excitation region using the high-frequency magnetic field with the initial irradiation frequency.

12. The magnetic resonance imaging apparatus according to claim 11, wherein the irradiation frequency setting section determines the first and second resonance frequencies corresponding to a shape of the spectral distribution of the resonance frequency of each of the materials.

13. The magnetic resonance imaging apparatus according to claim 10, wherein the irradiation frequency setting section determines the first and second resonance frequencies on the basis of an echo signal acquired from a local region in the two-dimensional excitation region.

14. The magnetic resonance imaging apparatus according to claim 13, wherein the control unit includes a magnetic field adjusting section which adjusts a static magnetic field strength of the local region to a predetermined value, and the irradiation frequency setting section determines the irradiation frequency on the basis of an echo signal acquired in a state where the static magnetic field strength of the local region has been adjusted to the predetermined value.

15. A two-dimensional excitation adjustment method in a magnetic resonance imaging apparatus which controls measurement of an echo signal generated from a two-dimensional excitation region of an object, which is placed in a static magnetic field and is formed by a first material with a first resonance frequency and a second material with a second resonance frequency, using a pulse sequence with a high-frequency magnetic field and a gradient magnetic field for performing two-dimensional excitation of the two-dimensional excitation region of the object, comprising:

an input step which inputs imaging conditions related to the two-dimensional excitation;

a step which calculates the first and second resonance frequencies;

a step which sets an irradiation frequency of the high-frequency magnetic field on the basis of the imaging conditions related to the two-dimensional excitation and the first and second resonance frequencies so that desired regions of the first and second materials are excited in a two-dimensional manner; and a step which sets an irradiation gain of the high-frequency magnetic field on the basis of an excitation angle of the two-dimensional excitation region and a frequency difference between the irradiation frequency and the first resonance frequency.

16. The two-dimensional excitation adjustment method according to claim 15, further comprising:

a step which sets a strength of the gradient magnetic field on the basis of a value of a parameter indicating a shape of the two-dimensional excitation region and a frequency difference between the irradiation frequency and the first resonance frequency.

17. A two-dimensional excitation adjustment method in a magnetic resonance imaging apparatus which controls measurement of an echo signal generated from a two-dimensional excitation region of an object, which is placed in a static magnetic field and is formed by a first material with a first resonance frequency and a second material with a second resonance frequency, using a pulse sequence with a high-frequency magnetic field and a gradient magnetic field for performing two-dimensional excitation of the two-dimensional excitation region of the object, comprising:

an input step which inputs imaging conditions related to the two-dimensional excitation;

a step which calculates the first and second resonance frequencies; and a step which sets an irradiation frequency of the high-frequency magnetic field on the basis of the imaging conditions related to the two-dimensional excitation and the first and second resonance frequencies so that desired regions of the first and second materials are excited in a two-dimensional manner, wherein the step which calculates the first and second resonance frequencies includes:

a step which acquires an echo signal from the two-dimensional excitation region using a high-frequency magnetic field with an initial irradiation frequency determined in advance;

a step which calculates a spectral distribution of the first and second resonance frequencies using the echo signal; and a step which determines the first and second resonance frequencies on the basis of the spectral distribution.

* * * * *